(12) United States Patent
Cui et al.

(10) Patent No.: US 7,696,343 B2
(45) Date of Patent: Apr. 13, 2010

(54) METHOD FOR OPENING TIGHT JUNCTIONS

(75) Inventors: Kunyuan Cui, Bothell, WA (US); Benjamin H Dutzar, Seattle, WA (US)

(73) Assignee: MDRNA, Inc., Bothell, WA (US)

( * ) Notice: Subject to any disclaimer, the term of this patent is extended or adjusted under 35 U.S.C. 154(b) by 163 days.

(21) Appl. No.: 11/624,630

(22) Filed: Jan. 18, 2007

(65) Prior Publication Data

US 2007/0253956 A1 Nov. 1, 2007

Related U.S. Application Data

(63) Continuation of application No. 11/009,868, filed on Dec. 10, 2004, now abandoned.

(60) Provisional application No. 60/529,682, filed on Dec. 15, 2003.

(51) Int. Cl.
*C07H 21/04* (2006.01)
*C07H 21/02* (2006.01)

(52) U.S. Cl. .................. 536/24.5; 536/23.1; 536/24.3; 536/24.33

(58) Field of Classification Search ............... 536/23.1, 536/24.3, 24.33
See application file for complete search history.

(56) References Cited

U.S. PATENT DOCUMENTS

| | | | |
|---|---|---|---|
| 5,554,388 A | 9/1996 | Illum | |
| 5,629,011 A | 5/1997 | Illum | |
| 5,744,166 A | 4/1998 | Illum | |
| 5,935,604 A | 8/1999 | Illum | |
| 6,048,536 A | 4/2000 | Chatfield | |
| 6,110,747 A | 8/2000 | Blaschuk et al. | |
| 6,136,606 A | 10/2000 | Chatfield | |
| 6,228,396 B1 | 5/2001 | Watts | |
| 6,248,864 B1 | 6/2001 | Blaschuk et al. | |
| 6,342,251 B1 | 1/2002 | Illum et al. | |
| 6,383,513 B1 | 5/2002 | Watts et al. | |
| 6,387,917 B1 | 5/2002 | Illum et al. | |
| 6,391,318 B1 | 5/2002 | Illum et al. | |
| 6,432,440 B1 | 8/2002 | Watts et al. | |
| 2002/0082391 A1 | 6/2002 | Anderson et al. | |
| 2003/0027761 A1 | 2/2003 | Blaschuk et al. | |
| 2005/0019314 A1 | 1/2005 | Bueno | |

FOREIGN PATENT DOCUMENTS

WO 0026360 A1 5/2000

(Continued)

OTHER PUBLICATIONS

Naik et al. (Arterioscler Thromb Vasc Biol. Dec. 23, 2003(12):2165-71. Epub Sep. 4, 2003).*

(Continued)

*Primary Examiner*—Sean McGarry
*Assistant Examiner*—Terra Cotta Gibbs
(74) *Attorney, Agent, or Firm*—Mark A. Bales; MDRNA, Inc.

(57) ABSTRACT

The use of antagonists to JAM-1 Claudin-4 and occludin to open tight junctions. The antagonists include, by way of example antibodies and antibody fragments that bind to the proteins and small interfering nucleic acids that downregulate the mRNA encoding the proteins.

6 Claims, 10 Drawing Sheets

FOREIGN PATENT DOCUMENTS

| | | |
|---|---|---|
| WO | 03000018 A2 | 1/2003 |
| WO | 03080021 | 10/2003 |
| WO | 03080022 | 10/2003 |
| WO | 2004003145 A2 | 1/2004 |
| WO | 2004062561 | 7/2004 |
| WO | 2004103396 A1 | 12/2004 |
| WO | 2005004895 A2 | 1/2005 |

OTHER PUBLICATIONS

Elbashir et al. (Methods, 2002 vol. 26:199-213).*
Liu et al. (J Cell Sci. Jul. 2000 113 ( Pt 13):2363-74).*
Armstrong et al, "Clinical Modulation of Oral Leukoplakia and Protease Activity by Bowman-Birk Inhibitor Concentrate in a Phase IIa Chemoprevention Trial," Clinical Cancer Research, Dec. 2000, vol. 6 No. 12, pp. 4684-4691.
Tomee et al, "Secretory leukoprotease inhibitor: a native antimicrobial protein presenting a new therapeutic option?" Thorax, Feb. 1998, vol. 53 No. 2, pp. 114-116.
Tomee et al, "Antileukoprotease: An Endogenous Protein in the Innate Mucosal Defense against Fungi," The Journal of Infectious Diseases, Sep. 1997, vol. 176 No. 3, pp. 740-747.
Rao et al, "Interaction of Secretory Leukocyte Protease Inhibitor with Proteinase-3," American Journal of Respiratory Cell and Molecular Biology, Jun. 1993, vol. 8 No. 6, pp. 612-616.
Thomson and Ohlsson, "Isolation, properties, and complete amino acid sequence of human secretory leukocyte protease inhibitor, a potent inhibitor of leukocyte elastase," Proc. Natl. Acad. Sci. USA, Sep. 1986, vol. 83 No. 18, pp. 6692-6696.
Farraj et al, "Nasal Administration of Insulin Using Bioadhesive Microspheres as a Delivery System," Journal of Controlled Release, 1990, vol. 13, pp. 253-261, Elsevier Science Publishers B.V., Amsterdam.
Llum et al, "Chitosan as a Novel Nasal Delivery System for Peptide Drugs," Pharmaceutical Research, 1994, vol. 11 No. 8, pp. 1186-1189, Plenum Publishing Corporation.
Coyne et al, "Enhanced Epithelial Gene Transfer by Modulation of Tight Junctions with Sodium Caprate," American Journal of Respiratory Cell and Molecular Biology, Nov. 2000, vol. 23, pp. 602-609, High Wire Press.
Ferruza et al, "Copper treatment alters the permeability of tight junctions in cultured human intestinal Caco-2 cells," American Journal of Physiology, Dec. 1999, 277 (6 Pt 1): G1138-1148.
Liu et al, "Dodecylphosphocholine-Mediated Enhancement of Paracellular Permeability and Cytotoxicity in Caco-2 Cell Monolayers," Journal of Pharmaceutical Sciences, Nov. 1999, vol. 88, No. 11, pp. 1161-1168.
Karlsson et al, "Paracellular drug transport across intestinal epithelia: influence of charge and induced water flux," European Journal of Pharmaceutical Sciences, Oct. 1999, vol. 9, No. 1, pp. 47-56.
Duizer et al, "Absorption Enhancement, Structural Changes in Tight Junctions and Cytoxicity Caused by Palmitoyl Carnitine in Caco-2 and IEC-18 Cells," The Journal of Pharmacology and Experimental Therapeutics, Oct. 1998, vol. 287, No. 1, pp. 395-402.
Brewster et al, "The Effect of Dihydronicotinate N-Substitution on the Brain-Targeting Efficacy of a Zidovudine Chemical Delivery System," Pharmaceutical Research, 1993, vol. 10, No. 9, pp. 1356-1362.
Drejer et al, "Intranasal Administration of Insulin With Phospholid as Absorption Enhancer: Pharmacokinetics in Normal Subjects," Diabetic Medicine, 1992, vol. 9, pp. 335-340.
Thanou et al, "Intestinal Absorption of Octreotide: N-Trimethyl Chitosan Chloride (TMC) Ameliorates the Permeability and Absorption Properties of the Somatostatin Analogue In vitro and In vivo," Journal of Pharmaceutical Sciences, Jul. 2000, vol. 89, No. 7, pp. 951-957.
Tamai and Tsuji, "Transporter-Mediated Permeation of Drugs Across the Blood-Brain Barrier," Journal of Pharmaceutical Sciences, Nov. 2000, vol. 89, No. 11, pp. 1371-1388.
Abbott, "Inflammatory Mediators and Modulation of Blood-Brain Barrier Permeability," Cellular and Molecular Neurobiology, Apr. 2000, vol. 20, No. 2, pp. 131-147, Plenum Publishing Corporation.
Lee et al, "Mucosal Penetration Enhancers For Facilitation of Peptide and Protein Drug Absorption," Critical Reviews in Therapeutic Drug Carrier Systems, 1991, vol. 8, No. 2, pp. 91-192, CRC Press, Inc.
Mishima et al, "Studies on the Promoting Effects of Medium Chain Fatty Acid Salts on the Nasal Absorption of Insulin in Rats," J. Pharmacobio-Dyn., 1987, vol. 10, pp. 624-631.
Nagai et al, "Powder Dosage Form of Insulin for Nasal Administration," Journal of Controlled Release, 1984, vol. 1, pp. 15-22, Elsevier Science Publishers B.V., Amsterdam, The Netherlands.
Rojanasakul et al, "The Transport Barrier of Epithelia: A Comparative Study on Membrane Permeability and Charge Selectivity in the Rabbit," Pharmaceutical Research, 1992, vol. 9, No. 8, pp. 1029-1034, Plenum Publishing Corporation.
Rydén and Edman, "Effect of polymers and microspheres on the nasal absorption of insulin in rats," International Journal of Pharmaceutics, 1992, vol. 83, pp. 1-10, Elsevier Science Publishers B.V.
Shen et al, "Calu-3: a human airway epithelial cell line that shows cAMP-dependent Cl- secretion," Am. J. Physiol, May 1994, vol. 266, No. 5 pt. 1, pp. L493-L501.
Uchimaya et al, "Effectiveness and Toxicity Screening of Various Absorption Enhancers in the Large Intestine: Intestinal Absorption of Phenol Red and Protein and Phospholipid Release from the Intestinal Membrane," Biol. Pharm. Bull., 1996, vol. 19. No. 12, pp. 1618-1621.
Uchimaya et al, "Effects of Various Protease Inhibitors on the Stability and Permeability of [D-Ala2, D-Leu5]enkephalin in the Rat Intestine: Comparison with Leucine Enkephalin," Journal of Pharmaceutical Sciences, Apr. 1998, vol. 87, No. 4, pp. 448-452.
Utoguchi et al, "Nitric Oxide Donors Enhance Rectal Absorption of Macromolecules in Rabbits," Pharmaceutical Research, 1998, vol. 15, No. 6, pp. 870-876, Plenum Publishing Corporation.
Watanabe et al, "Enhancing Effect of Cyclodextrins on Nasal Absorption of Insulin and Its Duration in Rabbits," Chem. Pharm. Bull., 1992, vol. 40, No. 11, pp. 3100-3104.
Yamamoto et al, "Effectiveness and Toxicity Screening of Various Absorption Enhancers in the Rat Small Intestine: Effects of Absorption Enhancers on the Intestinal Absorption of Phenol Red and the Release of Protein and Phospholids from the Intestinal Membrane," J. Pharm. Pharmacol., 1996, vol. 48, pp. 1285-1289.
Dreisin and Mostow, "Sulfhyryl-mediated depression of ciliary activity: an adverse effect of acetlycysteine," J. Lab. Clin. Med., Apr. 1979, vol. 93, No. 4, pp. 674-678.
Davies, "Biopharmaceutical Considerations in Topical Ocular Drug Delivery," Clinical and Experimental Pharmacology and Physiology, Jul. 2000, vol. 27, No. 7, pp. 558-562.
Torres-Lugo and Peppas, "Transmucosal delivery systems for calcitonin: a review," Biomaterials, Jun. 2000, vol. 21, No. 12, pp. 1191-1196, Elsevier.
Lim et al, "Preparation and evaluation of the in vitro drug release properties and mucoadhesion of novel microspheres of hyaluronic acid and chitosan," Journal of Controlled Release, May 2000, vol. 66, No. 2-3, pp. 281-292, Elsevier.
Huang et al, "Molecular aspects of muco- and bioadhesion: Tethered structures and site-specific surfaces," Journal of Controlled Release, Mar. 2000, vol. 65, No. 1-2, pp. 63-71, Elsevier.
Sugimoto et al, "Evaluation of Poly(vinyl alcohol)-Gel Spheres Containing Chitosan as Dosage Form to Control Gastrointestinal Transit Time of Drugs," Biol. Pharm. Bull., vol. 21, No. 11, pp. 1202-1206.
Watanabe et al, "Studies of Drug Delivery Systems for a Therapeutic Agent Used in Osteoporosis. II.1) Enhanced Absorption of Elcatonin from Nasal Mucosa in Rabbits2)," Nov. 1998, Biol. Pharm. Bull., vol. 21, No. 11, pp. 1191-1194.
Nielsen et al, "Bioadhesive drug delivery systems I. Characterization of mucoadhesive properties of systems based on glyceryl monolinoleate," European Journal of Pharmaceutical Sciences, Jul. 1998, vol. 6, No. 3, pp. 231-239, Elsevier.
Nair et al, "Biomembrane Permeation of Nicotine: Mechanistic Studies with Porcine Mucosae and Skin," Journal of Pharmaceutical Sciences, Feb. 1997, vol. 86, No. 2, pp. 257-262.

Bhat et al, "Drug Diffusion through Cystic Fibrotic Mucus: Steady-State Permeation, Rheologic Properties, and Glycoprotein Morphology," Journal of Pharmaceutical Sciences, Jun. 1996, vol. 85, No. 6, pp. 624-630.

Lehr, "From sticky stuff to sweet receptors—achievements, limits and novel approaches to bioadhesion," European Journal of Drug Metabolism and Pharmacokinetics, Apr.-Jun. 1996, vol. 21, No. 2, pp. 139-148.

Harris and Robinson, "Drug Delivery via the Mucous Membranes of the Oral Cavity," Journal of Pharmaceutical Sciences, Jan. 1992, vol. 81, No. 1, pp. 1-10.

Corbo et al, "Drug Absorption Through Mucosal Membranes: Effect of Mucosal Route and Penetrant Hydrophilicity," Pharmaceutical Research, Oct. 1989, vol. 6, No. 10, pp. 848-852.

Corbo et al, "Characterization of the Barrier Properties of Mucosal Membranes," Journal of Pharmaceutical Sciences, Mar. 1990, vol. 79, No. 3, pp. 202-206.

Wilson et al, "Applications of Endocytosis Research to Drug Delivery," Prog. Clin. Biol. Res., 1988, vol. 270, pp. 441-446.

Draghia et al, "Gene delivery into the central nervous system by nasal installation in rats," Gene Therapy, 1995, vol. 2, pp. 418-423, Stockton Press.

Sakane et al, "Direct drug transport from the rat nasal cavity to the cerebrospinal fluid: the relation to the dissociation of the drug," J. Pharm. Pharmacol., 1994, vol. 46, pp. 378-379.

Sakane et al, "Direct Drug Transport from the Rat Nasal Cavity to the Cerebrospinal Fluid: the Relation to the Molecular Weight of Drugs," J. Pharm. Pharmacol., 1995, vol. 47, pp. 379-381.

Seki et al, "Nasal Absorption of Zidovudine and Its Transport to Cerebrospinal Fluid," Biol. Pharm. Bull., Aug. 1994, vol. 17, No. 8, 1135-1137.

Thorne et al, "Quantitative analysis of the olfactory pathway for drug delivery to the brain," Brain Research, 1995, vol. 692, pp. 278-282, Elsevier Science B.V.

Lukacs et al, "Constitutive internalization of cystic fibrosis transmembrane conductance regulator occurs via clathrin-dependent endocytosis and is regulated by protein phosphorylation," Biochem J., Dec. 1997, vol. 328, pp. 353-361.

Adson et al, "Quantitative Approaches to Delineate Paracellular Diffusion in Cultured Epithelial Cell Monolayers," Journal of Pharmaceutical Sciences, Nov. 1994, vol. 83, No. 11, pp. 1529-1536.

Adson et al, "Passive Diffusion of Weak Organic Electrolytes across Caco-2 Cell Monolayers: Uncoupling the Contributions of Hydrodynamic, Transcellular, and Paracellular Barriers," Journal of Pharmaceutical Sciences, Oct. 1995, vol. 84, No. 10, pp. 1197-1204.

Balboni et al, "Immunohistochemical Detection of EGF and NGF Receptors in Human Olfactory Epithelium," Boll. Soc. It. Biol. Sper., 1991, No. 10/11, vol. LXVII, Idelson, Naples, Italy.

Deckner et al, "Localization of neurotrophin receptors in olfactory epithelium and bulb," NeuroReport, Dec. 1993, vol. 5, No. 3, pp. 301-304.

Ferkol et al, "Gene Transfer into Respiratory Epithelial Cells by Targeting the Polymeric Immunoglobulin Receptor," J. Clin. Invest., Nov. 1993, vol. 92, pp. 2394-2400.

Lamaze and Schmid, "The emergence of clathrin-independent pinocytic pathways," Current Opinion in Cell Biology, 1995, vol. 7, pp. 573-580.

Langer, "Selected advances in drug delivery and tissue engineering," Journal of Controlled Release, Nov. 1999, vol. 62, No. 1-2, pp. 7-11, Elsevier Science B.V.

Huter et al, "Bacterial ghosts as drug carrier and targeting vehicles," Journal of Controlled Release, Aug. 1999, vol. 61, No. 1-2, pp. 51-63, Elsevier Science B.V.

Reddy and Low, "Folate-Mediated Targeting of Therapeutic and Imaging Agents to Cancers," Critical Reviews in Therapeutic Drug Carrier Systems, 1998, vol. 15, No. 6, pp. 587-627.

Holladay et al, "Riboflavin-mediated delivery of a macromolecule into cultured human cells," Biochimica et Biophysica Acta, Jan. 1999, vol. 1426, No. 1, pp. 195-204, Elsevier Science B.V.

Pardridge et al, "Enhanced Endocytosis in Cultured Human Breast Carcinoma Cells and In Vivo Biodistribution in Rats of a Humanized Monoclonal Antibody after Cationization of the Protein," The Journal of Pharmacology and Experimental Therapeutics, Jul. 1998, vol. 286, No. 1, pp. 548-554.

Swaan, "Recent Advances in Intestinal Macromolecular Drug Delivery via Receptor-Mediated Transport Pathways," Pharmaceutical Research, Jun. 1998, vol. 15, No. 6, pp. 826-834, Plenum Publishing Corporation.

Hope et al, "Cationic lipids, phosphatidylethanolamine and the intracellular delivery of polymeric, nucleic acid-based drugs (Review)," Molecular Membrane Biology, Jan.-Mar. 1998, vol. 15, No. 1, pp. 1-14.

Konigsberg et al, "The development of IL-2 conjugated liposomes for therapeutic purposes," Biochimica et Biophysica Acta, Mar. 1998, vol. 1370, No. 2, pp. 243-251, Elsevier Science B.V.

Wu et al, "Development of a Novel Drug-Delivery System Using Bacterio-Phage MS2 Capsids," Biochemical Society Transactions, Aug. 1996, vol. 24, No. 3, p. 413S.

Nomura et al, "Effect of Histamine on the Blood-Tumor Barrier in Transplanted Rat Brain Tumors," Acta Neurochir, 1994, vol. 60, pp. 400-402.

Kirsten et al, "Clinical Pharmacokinetics of Vasodilators," Clin. Pharmacokinet., Jun. 1998, vol. 34, No. 6, pp. 457-482.

Waxman et al, "Persistent Primary Coronary Dilation Induced by Transatrial Delivery of Nitroglycerin Into the Pericardial Space: A Novel Approach for Local Cardiac Drug Delivery," Journal of the American College of Cardiology, Jun. 1999, vol. 33, No. 7, pp. 2073-2077, Elsevier Science Inc.

Cornfield et al, "Aerosol delivery of diethylenetriamine/nitric oxide, a nitric oxide adduct, causes selective pulmonary vasodilation in perinatal lambs," J. Lab. Clin. Med., Oct. 1999, vol. 134, No. 4, pp. 419-425.

Putensen et al, "Cardiopulmonary Effects of Aerosolized Prostaglandin E1 and Nitric Oxide Inhalation in Patients with Acute Respiratory Distress Syndrome," Am. J. Respir. crit. Care Med., Jun. 1998, vol. 157, No. 6 Pt 1, pp. 1743-1747.

Kato and Sugiyama, Targeted Delivery of Peptides, Proteins, and Genes by Receptor-Mediated Endocytosis, Critical Reviews in Therapeutic Drug Carrier Systems, 1997, vol. 14, No. 3, pp. 287-331.

Takahashi et al, "The Enhancing Mechanism of Capric Acid (C10) from a Suppository on Rectal Drug Absorption through a Paracellular Pathway," Biol. Pharm. Bull., 1994, vol. 20, No. 4, pp. 446-448.

Boek et al, "Validation of Animal Experiments on Ciliary Function In Vitro. II. The Influence of Absorption Enhancers, Preservatives and Physiologic Saline," Acta Otolaryngol, Jan. 1999, vol. 119, No. 1, pp. 98-101, Scandinavian University Press, Stockholm.

Boek et al, "Physiologic and Hypertonic Saline Solutions Impair Ciliary Activity in Vitro," Laryngoscope, Mar. 1999, vol. 109, No. 3, pp. 396-399, Lippincott Williams & Wilkins, Inc., Philadelphia.

Karttunen et al, "The Effects of Vadocaine, Dextromethorphan, Diphenhydramine, and Hydroxyzine on the Ciliary Beat Frequency in Rats in Vitro," Pharmacology & Toxicology, Aug. 1990, vol. 62, No. 2, pp. 159-161.

Hermens et al, "Effects of Absorption Enhancers on Human Nasal Tissue Ciliary Movement in Vitro," Pharmaceutical Research, Feb. 1990, vol. 7, No. 2, pp. 144-146.

Chien, Transnasal Systemic Medications. Fundamentals, Developmental Concepts and Biomedical Assessments, 1985, Elsevier Science, Amsterdam.

Cevc, "Transfersomes, Liposomes and Other Lipid Suspensions on the Skin: Permeation Enhancement, Vesicle Penetration, and Transdermal Drug Delivery," Critical Reviews in Therapeutic Drug Carrier Systems, 1996, vol. 13, No. 3-4, pp. 257-388.

Kuo and Saltzman, "Novel Systems for Controlled Delivery of Macromolecules," Critical Reviews in Eukaryotic Gene Expression, 1996, vol. 6, No. 1, pp. 59-73.

Aurrand-Lions, M.; Duncan, L.; Ballestrem, C.; and Imhof, B. A.; "JAM-2, a Novel Immunoglobulin Superfamily Molecule, Expressed by Endothelial and Lymphatic Cells;" J Biol Chem; Jan. 2001; 276 (4); 2733-2741.

Nusrat et al., "Human Junctional Adhesion Molecule Regulates Tight Junction Structure and Paracellular Permeability in Intestinal Epithelia," Gastroenterology, Apr. 2000, vol. 188, No. 4 Suppl. 2 part 1, p. AGA A432. Abstract. ISSN: 0016:5085.

Johnson et al., "Exploiting Tight Junctions for Delivery of Drugs," Genetic Engineering News, vol. 24, No. 1, Jan. 2004, p. 34.

Eppstein and Longenecker, "Alternative Delivery Systems for Peptides and Proteins as Drugs," CRC Crit. Rev. Ther. Drug Carrier Syst., 1988, vol. 5, issue 2, pp. 99-139.

Longenecker et al, "Effects of Sodium Taurodihydrofusidate on Nasal Absorption of Insulin in Sheep," Journal of Pharmaceutical Science, 1987, vol. 76, pp. 351-355.

Boek et al, "Validation of Animal Experiments on Ciliary Function In Vitro. I. The Influence of Substances Used Clinically," Acta Otolaryngol, Jan. 1999, vol. 119, No. 1, pp. 93-97, Scandinavian University Press, Stockholm.

Hingley et al, "Effect of Ciliostatic Factors from *Pseudomonas aeruginosa* on Rabbit Respiratory Cilia," Infection and Immunity, Jan. 1986, vol. 51, No. 1, pp. 254-262.

Gabridge et al, "Effects of Heavy Metals on Structure, Function, and Metabolism of Ciliated Respiratory Epithelium In Vitro," In Vitro, Dec. 1982, vol. 18, No. 12, pp. 1023-1032.

Yamamoto et al, "Modulation of Intestinal Permeability by Nitric Oxide Donors: Implications in Intestinal Delivery of Poorly Absorbable Drugs," The Journal of Pharmacology and Experimental Therapeutics, 2001, vol. 296, No. 1, pp. 84-90.

Henriksson et al, "Calculation of the isoelectric points of native proteins with spreading of pKa values," Electrophoresis, vol. 16, No. 8, pp. 1377-1380.

Wolfert et al, "Polyelectrolyte Vectors for Gene Delivery: Influence of Cationic Polymer on Biophysical Properties of Complexes Formed with DNA," Bioconjugate Chem., Nov.-Dec. 1999, vol. 10, No. 6, pp. 993-1004.

Pade and Stavchansky, "Estimation of the Relative Contribution of the Transcellular and Paracellular Pathway to the Transport of Passively Absorbed Drugs in the Caco-2 Cell Culture Model," Pharmaceutical Research, Sep. 1997, vol. 14, No. 9, pp. 1210-1215, Plenum Publishing Company.

Murakami et al, "Role of the Dispersion Systems Containing Fusogenic Lipids on the Enhanced Absorption of Poorly Absorbable Drugs from the Gastrointestinal Tract," Journal of Pharmacobio-Dyn., 1985, vol. 8, s-131, p. 49.

Muranishi, "Absorption Enhancers," Crit. Rev. Ther. Drug Carrier Syst., 1990, vol. 7, issue 1, pp. 1-33.

Tozaki et al, "Enhanced Absorption of Insulin and (Asu1,7)Eel-Calcitonin using Novel Azopolymer-Coated Pellets for Colon-Specific Drug Delivery," Journal of Pharmaceutical Sciences, Jan. 2001, vol. 90, No. 1, pp. 89-97.

Senel et al, "Enhancing effect of chitosan on peptide drug delivery across buccal mucosa," Biomaterials, Oct. 2000, vol. 21, No. 20, pp. 2067-2071, Elsevier Science Ltd.

Marschütz and Bernkop-Schnürch, "Oral peptide drug delivery: polymer-inhibitor conjugates protecting insulin from enzymatic degradation in vitro," Biomaterials, Jul. 2000, vol. 21, No. 14, pp. 1499-1507.

Bernkop-Schnürch and Thaler, "Polycarbophil-Cysteine Conjugates as Platforms for Oral Polypeptide Delivery Systems," Journal of Pharmaceutical Sciences, Jul. 2000, vol. 89, No. 7, pp. 901-909.

Ali et al, "Transferrin Trojan Horses as a Rational Approach for the Biological Delivery of Therapeutic Peptide Domains," The Journal of Biological Chemistry, Aug. 1999, vol. 274, No. 34, pp. 24066-24073.

Bernkop-Schnürch, "The use of inhibitory agents to overcome the enzymatic barrier to perorally administered therapeutica peptides and proteins," Journal of Controlled Release, Mar. 1998, vol. 52, No. 1-2, pp. 1-16, Elsevier Science B.V.

Kratzel et al, "Auxiliary Agents for the Peroral Administration of Peptide and Protein Drugs: Synthesis and Evaluation of Novel Pepstatin Analogues," J. Med. Chem., Jun. 1998, vol. 41, No. 13, pp. 2339-2344.

Bai et al, "Effects of Polyacrylic Polymers on the Degradation of Insulin and Peptide Drugs by Chymotrypsin and Trypsin," J. Pharm. Pharmacol., Jan. 1996, vol. 48, No. 1, pp. 17-21.

Ekrami et al, "Disposition of Positively Charged Bowman-Birk Protease Inhibitor Conjugates in Mice: Influence of Protein Conjugate Charge Density and Size on Lung Targeting," Journal of Pharmaceutical Sciences, Apr. 1995, vol. 84, No. 4, pp. 456-461.

Marston and Hartley, "Solubilization of Protein Aggregates," Methods in Enzymology, vol. 182, No. 1, pp. 264-276.

Daugherty and Gellman, "A Flourescence Assay for Leucine Zipper Dimerization: Avoiding Unintended Consequences of Fluorophore Attachment," J. Am. Chem. Soc., 1999, vol. 121, pp. 4325-4333.

Daugherty and Gellman, "A Flourescence Assay for Leucine Zipper Dimerization: Avoiding Unintended Consequences of Fluorophore Attachment," J. Am. Chem. Soc., 1999, vol. 121, pp. 4325-4333.

Fan et al, "Inhibition of HIV-1 Protease by a Subunit of Didemnaketal A," J. Am. Chem. Soc., 1998, vol. 120, pp. 8893-8894.

Gamboni et al, "Inhibition of the cAMP-Dependent Protein Kinase by Synthetic A-Helix Peptides," Biochemistry, 1998, vol. 37, pp. 12189-12194.

Khan et al, "Solubilization of Recombinant Ovine Growth Hormone with Retention of Native-like Secondary Structure and Its Refolding from the Inclusion Bodies of *Escherichia coli*," Biotechnol. Prog., Sep.-Oct. 1997, vol. 14, No. 5, pp. 722-728.

Kendrick et al, "Aggregation of Recombinant Human Interferon Gamma: Kinetics and Structural Transitions," Journal of Pharmaceutical Sciences, Sep. 1998, vol. 87, No. 9, pp. 1069-1076.

Kopito, "Aggresomes, inclusion bodies and protein aggregation," Trends in Cell Biology, Dec. 2000, vol. 10, No. 12, pp. 524-530.

Futaki et al, "Arginine-rich Peptides. An Abundant Source of Membrane-Permeable Peptides Having Potential as Carriers for Intracellular Protein Delivery," The Journal of Biological Chemistry, Feb. 2001, vol. 276, No. 8, pp. 5836-5840.

Lai et al, "Intercellular delivery of a herpes simplex virus VP22 fusion protein from cells infected with lentiviral vectors," Proc. Natl. Acad. Sci. USA, Oct. 2000, vol. 97, No. 21, pp. 11297-11302.

Meyenburg et al, "Fibrin encapsulated liposomes as protein delivery system Studies on the in vitro release behavior," Journal of Controlled Release, Oct. 2000, vol. 69, No. 1, pp. 159-168, Elsevier Science B.V.

Tobío et al, "The role of PEG on the stabilty in digestive fluids and in vivo fate of PEG-PLA nanoparticles following oral administration," Colloids and Surfaces B: Biointerfaces, Oct. 2000, vol. 18, No. 3-4, pp. 315-323.

Bezemer et al, "Microspheres for protein delivery prepared from amphiphilic multiblocks copolymers. 1. Influence of preparation techniques on particle characteristics and protein delivery," Journal of Controlled Release, Jul. 2000, vol. 67, No. 2-3, pp. 233-248, Elsevier Science B.V.

Bezemer et al, "Microspheres for protein delivery prepared from amphiphilic multiblock copolymers. 2. Modulation of release rate," Journal of Controlled Release, Jul. 2000, vol. 67, No. 2-3, pp. 249-260, Elsevier Science B.V.

Guillaume et al, "Phosphonocationic Lipids in Protein Delivery to Mice Lungs," Journal of Pharmaceutical Sciences, May 2000, vol. 89, No. 5, pp. 639-645.

Galán and Collmer, "Type III Secretion Machines: Bacterial Devices for Protein Delivery into Host Cells," Science, May 1999, vol. 284, No. 5418, pp. 1322-1328.

Witschi and Mrsny, "In Vitro Evaluation of Microparticles and Polymer Gels for Use as Nasal Platforms for Protein Delivery," Pharmaceutical Research, Mar. 1999, vol. 16, No. 3, pp. 382-390.

Crotts and Park, "Protein delivery from poly(lactic-co-glycolic acid) biodegradable microspheres: release kinetics and stability issues," J. Microencapsulation, 1998, vol. 15, No. 6, pp. 699-713.

Coombes et al, "The control of protein release from poly(DL-lactide CO-glycide) microparticles by variation of the external aqueous phase surfactant in the water-in oil-in water method," Journal of Controlled Release, Mar. 1998, vol. 52, pp. 311-320.

Bernkop-Schnürch and Pasta, "Intestinal Peptide and Protein Delivery: Novel Bioadhesive Drug-Carrier Matrix Shielding from Enzymatic Attack," Journal of Pharmaceutical Sciences, Apr. 1998, vol. 87, No. 4, pp. 430-434.

Chiba et al, "Controlled protein delivery from biodegradable tyrosine-containing poly(anhydride-co-imide) microspheres," Biomaterials, Jul. 1997, vol. 18, No. 13, pp. 893-901.

Moy et al, "Tat-Mediated Protein Delivery Can Facilitate MHC Class I Presentation of Antigens," Molecular Biotechnology, Oct. 1996, vol. 6, No. 2, pp. 105-113.

Anderberg et al, "Sodium Caprate Elicits Dilations in Human Intestinal Tight Junctions and Enhances Drug Absorption by the Paracellular Route," Pharmaceutical Research, 1993, vol. 10, No. 6, pp. 857-864, Plenum Publishing Corporation.

Bernkop-Schnürch et al, "Peroral Polypeptide Delivery," Arzneimittelforschung, Sep. 1999, vol. 49, No. 9, pp. 799-803.

Boado et al, "Drug Delivery of Antisense Molecules to the Brain for Treatment of Alzheimer's Disease and Cerebral AIDS," Journal of Pharmaceutical Sciences, Nov. 1998, vol. 87, No. 11, pp. 1308-1315.

Broglia et al, "Folding and aggregation of designed proteins," Proc. Natl. Acad. Sc., Oct. 1998, vol. 95, No. 22, pp. 12930-12933.

Cremaschi et al, "Endocytosis of Polypeptides in Rabbit Nasal Respiratory Mucosa," News Physiol. Sci., Oct. 1997, vol. 12, pp. 219-225.

Elbert et al, "Monolayers of Human Alveolar Epithelial Cells in Primary Culture for Pulmonary Absorption and Transport Studies," Pharmaceutical Research, May 1999, vol. 16, No. 5, pp. 601-608.

Fasano and Uzzau, "Modulation of Intestinal Tight Junctions by Zonula Occludens Toxin Permits Enteral Administration of Insulin and Other Macromolecules in an Animal Model," J. Clin. Invest., Mar. 1997, vol. 99, No. 6, pp. 1158-1164.

Fasano, "Modulation of Intestinal Permeability: an Innovative Method of Oral Drug Delivery for the Treatment of Inherited and Acquired Human Diseases," Molecular Genetics and Metabolism, May 1998, vol. 64, pp. 12-18, Academic Press.

Fisher et al, "Effect of L--lysophosphatidylcholine on the nasal absorption of human growth hormone in three animal species," International Journal of Pharmaceutics, 1991, vol. 74, pp. 147-156, Elsevier Science Publishers B.V.

Ghosh and Chmielewski, "A betas-sheet peptide inhibitor of E47 dimerization and DNA binding," Chem. Biol., Aug. 1998, vol. 5, pp. 439-445.

Halmos et al, "Synthesis of -methylsulfonyl derivatives of D-glucose as potential alkylating agents for targeted drug delivery to the brain. Evaluation of their interaction with the human erythrocyte GLUT1 hexose transporter," Carbohydrate Research, 1997, vol. 299, pp. 15-21, Elsevier.

Hirai et al, "Mechanisms for the enhancement of the nasal absorption of insulin by surfactants," International Journal of Pharmaceuticals, 1981, vol. 9, pp. 173-184, Elsevier/North-Holland Biomedical Press.

Hochman and Artursson, "Mechanisms of absorption enhancement and tight junction regulation," Journal of Controlled Release, 1994, vol. 29, pp. 253-267.

Illum et al, "Bioadhesive microspheres as a potential nasal drug delivery system," International Journal of Pharmaceutics, 1987, vol. 39, pp. 189-199, Elsevier Science Publishers B.V.

Jacobs et al, "The Pharmacodynamics and Activity of Intranasally Administered Insulin in Healthy Male Volunteers," Diabetes, Nov. 1993, vol. 42, pp. 1649-1655.

Judice et al, "Inhibition of HIV type 1 infectivity by constrained alpha-helical peptides: Implications for the viral fusion mechanism," Proc. Natl. Acad. Sci., Dec. 1997, vol. 94, pp. 13426-13430.

Leung et al, "Selective disruption of protein aggregation by cyclodextrin dimers," Proc Natl. Acad. Sci., May 2000, vol. 97, No. 10, pp. 5050-5053.

Lewis et al, "PMA alters folate receptor distribution in the plasma membrane and increases the rate of 5-methyltetrahydrofolate delivery in mature MA104 cells," Biochimica et Biophysica Acta, 1998, vol. 1401, pp. 157-169.

Liu et al, "Structure-Activity Relationships for Enhancement of Paracellular Permeability by 2-Alkoxy-3-alkylamidopropylphosphocholines across Caco-2 Cell Monolayers," Journal of Pharmaceutical Sciences, Nov. 1999, vol. 88, No. 11, pp. 1169-1174.

Nagai et al, "Inhibition of Polyglutamine Protein Aggregation and Cell Death by Novel Peptides Identified by Phage Display Screening," The Journal of Biological Chemistry, Apr. 2000, vol. 275, No. 14, pp. 10437-10442.

NAM et al, "Lysozyme Microencapsulation Within Biodegradable PLGA Microspheres: Urea Effect on Protein Release and Stability," Biotechnol. Bioeng., Nov. 2000, vol. 70, No. 3, pp. 270-277.

Negri et al, "Glycodermorphins: opioid peptides with potent and prolonged analgesic activity and enhanced blood-brain barrier penetration," British Journal of Pharmacology, 1998, vol. 124, pp. 1516-'1522, Stockton Press.

Pardridge, "New approaches to drug delivery through the blood-brain barrier," Trends in Biotechnology, 1994, vol. 12, pp. 239-245, Elsevier Science Ltd., Cambridge, UK.

Park et al, "Protein Surface Recognition by Synthetic Receptors: A Route to Novel Submicromolar Inhibitors for -Chymotrypsin," J. Am. Chem. Soc., 1999, vol. 121, pp. 8-13.

Polt et al, "Glycopeptide enkephalin analogues produce analgesia in mice: Evidence for penetration of the blood-brain barrier," Proc. Natl. Acad. Sci. USA, Jul. 1994, vol. 91, pp. 7114-7118, Pharmacology.

Salartash et al, "Oral low-molecular weight heparin and delivery agent prevents jugular venous thrombosis in the rat," J. Vasc. Surg., Sep. 1999, vol. 30, No. 3, pp. 526-531.

Tamai et al, "Structure-Internalization Relationship for Adsorptive-Mediated Endocytosis of Basic Peptides at the Blood-Brain Barrier," the Journal of Pharmacology and Experimental Therapeutics, 1997, vol. 280, No. 1, pp. 410-415.

Tsuzuki et al, "Adamantane as a Brain-Directed Drug Carrier for Poorly Absorbed Drug. 2. AZT Derivatives Conjugated with the 1-Adamantane Moiety," Journal of Pharmaceutical Sciences, Apr. 1994, vol. 83, No. 4, pp. 481-484.

Uchimaya et al, "Enhanced Permeability of Insulin across the Rat Intestinal Membrane by Various Absorption Enhancers: Their Intestinal Mucosa! Toxicity and Absorption-enhancing Mechanism of n-Lauryl-D-maltopyranoside," J. Pharm. Pharmacol., Nov. 1999, vol. 51, No. 11, pp. 1241-1250.

Vawter et al, "Human Olfactory Neuroepithelial Cells: Tyrosine Phosphorylation and Process Extension Are Increased by the Combination of IL-1, IL-6, NGF, and bFGF," Experimental Neurology, 1996, vol. 142, pp. 179-194 (Article No. 0189).

Wakamiya et al, "Design and Synthesis of Peptides Passing through the Blood-Brain Barrier," Bull. Chem. Soc. Jpn., 1998, vol. 71, pp. 699-709.

Zutshi et al, "Targeting the Dimerization Interface of HIV-1 Protease: Inhibition with Cross-Linked Interfacial Peptides," J. Am. Chem. Soc., 1997, vol. 119, pp. 4841-4845.

* cited by examiner

METHOD FOR OPENING TIGHT JUNCTIONS

This application is a continuation and claims priority under 35 U.S.C. §120 of U.S. application Ser. No. 11/009,868, filed Dec. 10, 2004, and claims the benefit under 35 U.S.C. §119(e) of U.S. Provisional Patent Application Ser. No. 60/529,682 filed on Dec. 15, 2003, the entire contents of which is incorporated by reference.

BACKGROUND OF THE INVENTION

The teachings of all of the references cited herein are incorporated in their entirety by reference.

A major disadvantage of drug administration by injection is that trained personnel are often required to administer the drug. For self-administered drugs, many patients are reluctant or unable to give themselves injections on a regular basis. Injection is also associated with increased risks of infection. Other disadvantages of drug injection include variability of delivery results between individuals, as well as unpredictable intensity and duration of drug action.

Despite these noted disadvantages, injection remains the only approved delivery mode for a many important therapeutic compounds. These include conventional drugs, as well as a rapidly expanding list of peptide and protein biotherapeutics. Delivery of these compounds via alternate routes of administration, for example, oral, nasal and other mucosal routes, often yields variable results and adverse side effects, and fails to provide suitable bio-availability. For macromolecular species in particular, especially peptide and protein therapeutics, alternate routes of administration are limited by susceptibility to inactivation and poor absorption across mucosal barriers.

Mucosal administration of therapeutic compounds may offer certain advantages over injection and other modes of administration, for example in terms of convenience and speed of delivery, as well as by reducing or elimination compliance problems and side effects that attend delivery by injection. However, mucosal delivery of biologically active agents is limited by mucosal barrier functions and other factors. For these reasons, mucosal drug administration typically requires larger amounts of drug than administration by injection. Other therapeutic compounds, including large molecule drugs, peptides and proteins, are often refractory to mucosal delivery.

The ability of drugs to permeate mucosal surfaces, unassisted by delivery-enhancing agents, appears to be related to a number of factors, including molecular size, lipid solubility, and ionization. Small molecules, less than about 300-1,000 Daltons, are often capable of penetrating mucosal barriers, however, as molecular size increases, permeability decreases rapidly. Lipid-soluble compounds are generally more permeable through mucosal surfaces than are non-lipid-soluble molecules. Peptides and proteins are poorly lipid soluble, and hence exhibit poor absorption characteristics across mucosal surfaces.

In addition to their poor intrinsic permeability, large macromolecular drugs, including proteins and peptides, are often subject to limited diffusion, as well as lumenal and cellular enzymatic degradation and rapid clearance at mucosal sites. These mucosal sites generally serve as a first line of host defense against pathogens and other adverse environmental agents that come into contact with the mucosal surface. Mucosal tissues provide a substantial barrier to the free diffusion of macromolecules, while enzymatic activities present in mucosal secretions can severely limit the bioavailability of therapeutic agents, particularly peptides and proteins. At certain mucosal sites, such as the nasal mucosa, the typical residence time of proteins and other macromolecular species delivered is limited, e.g., to about 15-30 minutes or less, due to rapid mucociliary clearance.

In summary, previous attempts to successfully deliver therapeutic compounds, including small molecule drugs and protein therapeutics, via mucosal routes have suffered from a number of important and confounding deficiencies. These deficiencies point to a long-standing unmet need in the art for pharmaceutical formulations and methods of administering therapeutic compounds that are stable and well tolerated and that provide enhanced mucosal delivery, including to targeted tissues and physiological compartments such as central nervous system. More specifically, there is a need in the art for safe and reliable methods and compositions for mucosal delivery of therapeutic compounds for treatment of diseases and other adverse conditions in mammalian subjects. A related need exists for methods and compositions that will provide efficient delivery of macromolecular drugs via one or more mucosal routes in therapeutic amounts, which are fast acting, easily administered and have limited adverse side effects such as mucosal irritation or tissue damage.

In relation to these needs, an especially challenging need persists in the art for methods and compositions to enhance mucosal delivery of biotherapeutic compounds that will overcome mucosal epithelial barrier mechanisms. Selective permeability of mucosal epithelia has heretofore presented major obstacles to mucosal delivery of therapeutic macromolecules, including biologically active peptides and proteins. Accordingly, there remains a substantial unmet need in the art for new methods and tools to facilitate mucosal delivery of biotherapeutic compounds. In particular, there is a compelling need in the art for new methods and formulations to facilitate mucosal delivery of biotherapeutic compounds that have heretofore proven refractory to delivery across mucosal barriers.

DESCRIPTION OF THE INVENTION

Figure 1:
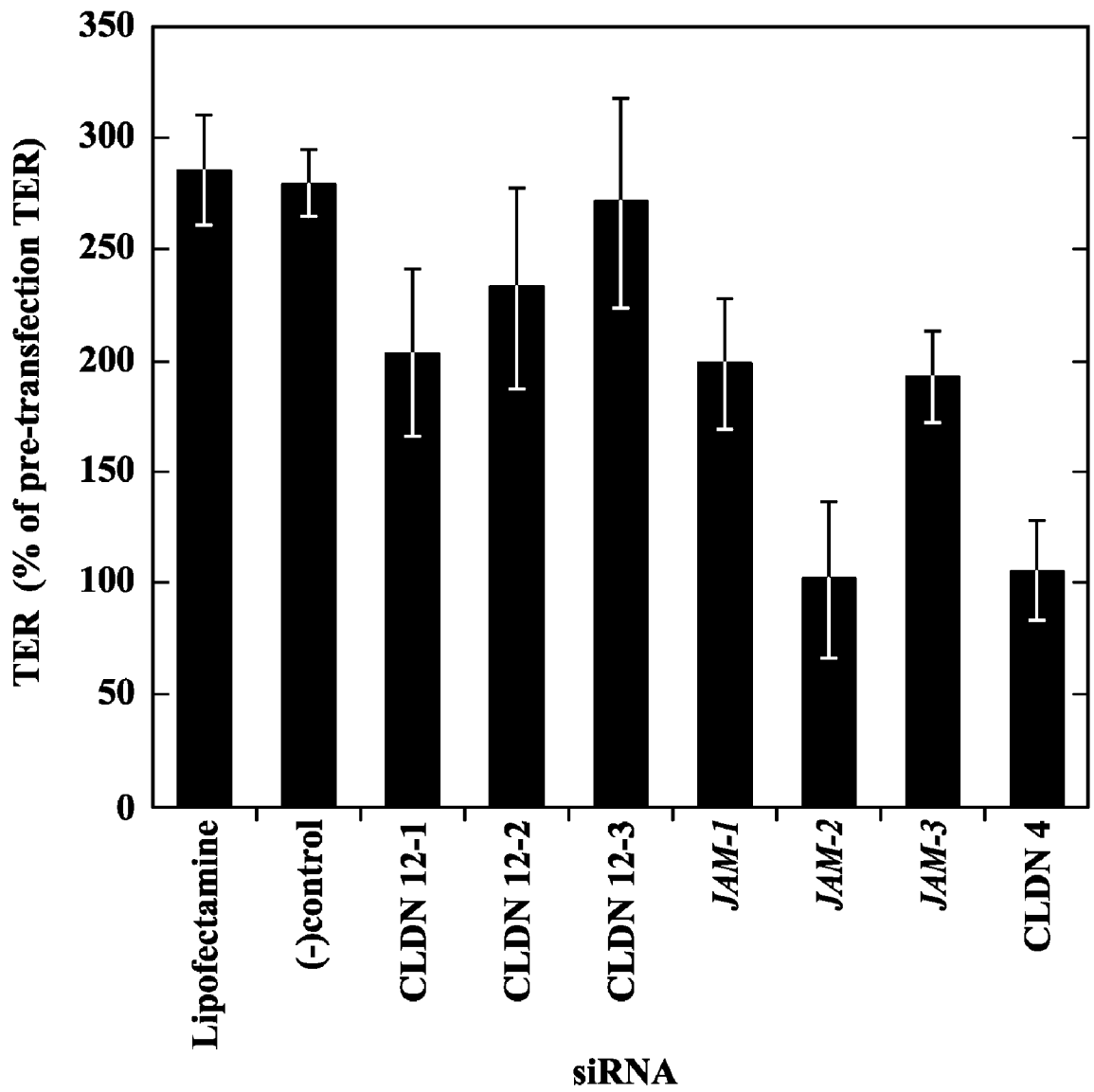
FIG. 1. Screening siRNAs against TJ proteins identifies those that affect TER. Three siRNAs against each TJ protein expressed in respiratory cells were designed and chemically synthesized. The effects on TER were monitored before and after transfections. The figure is an example of the screening of siRNAs against CLDN 12 and JAM-1. The siRNA against CLDN 4 was used as a positive control. The best candidates showing maximum effect were used for determining the extent of mRNA reduction by the bDNA method.
Figure 2A:
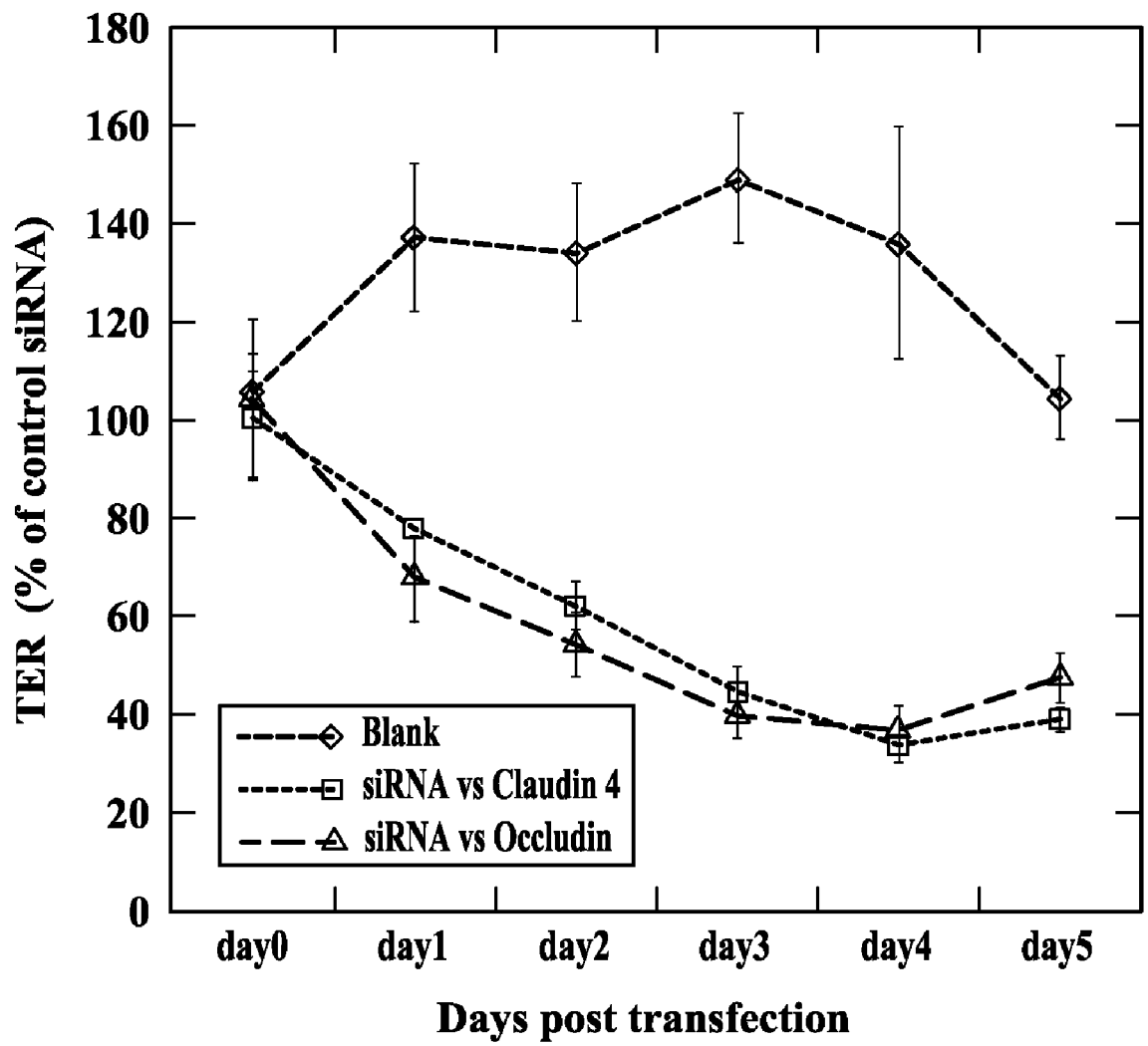
FIG. 2. Time Course of Specific siRNAs and Lipofectamine alone (blank) on TER. (A) The percent of TER, normalized against control siRNA at each time point. Effects of the transfection reagent (lipofectamine) on TER can be corrected. (B) Although the negative effects on TER by transfection procedure and reagents (blank) are observed, the TER value returns to normal after 3-4 days of transfection.
Figure 2B:
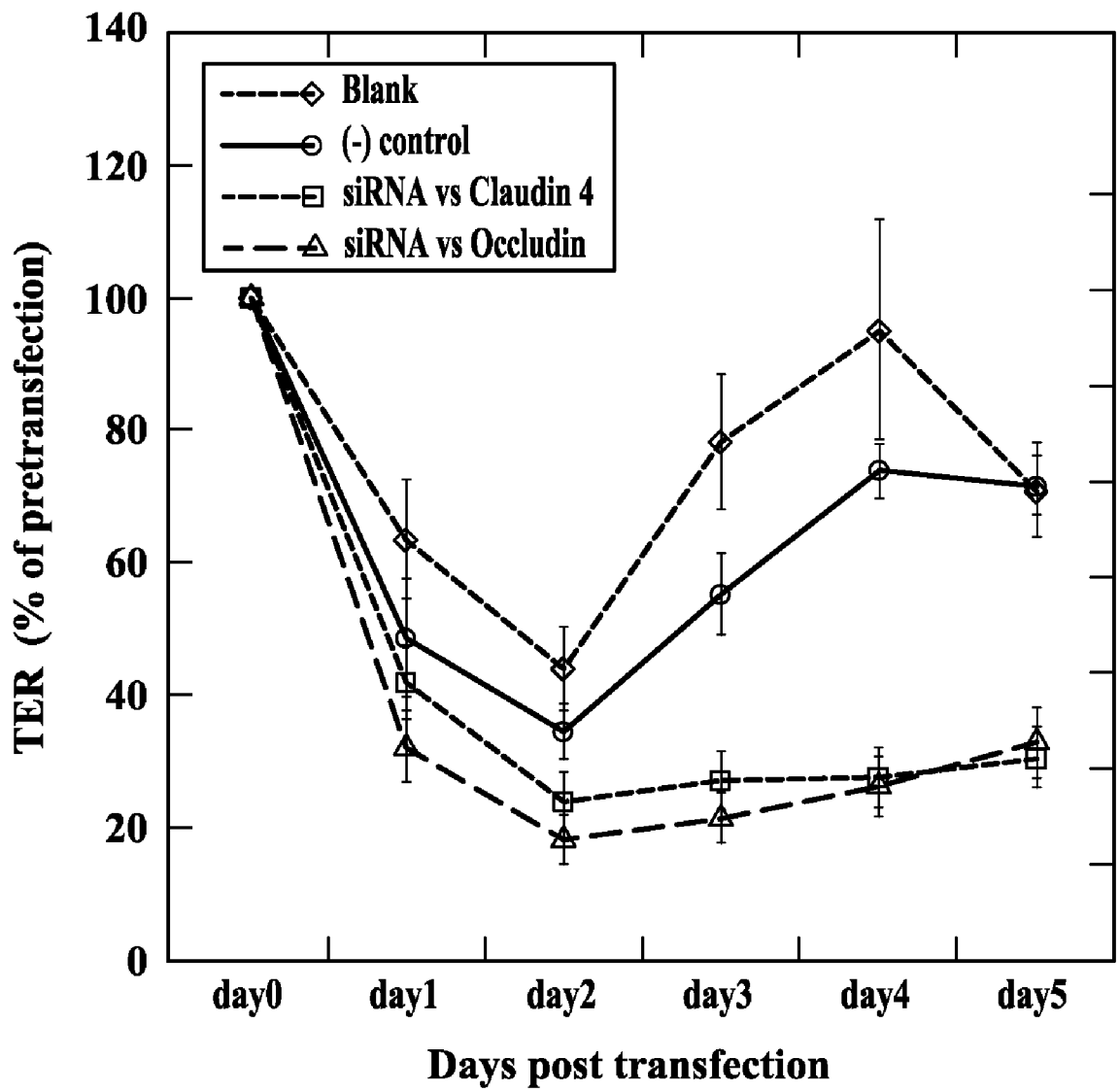
Figure 3:
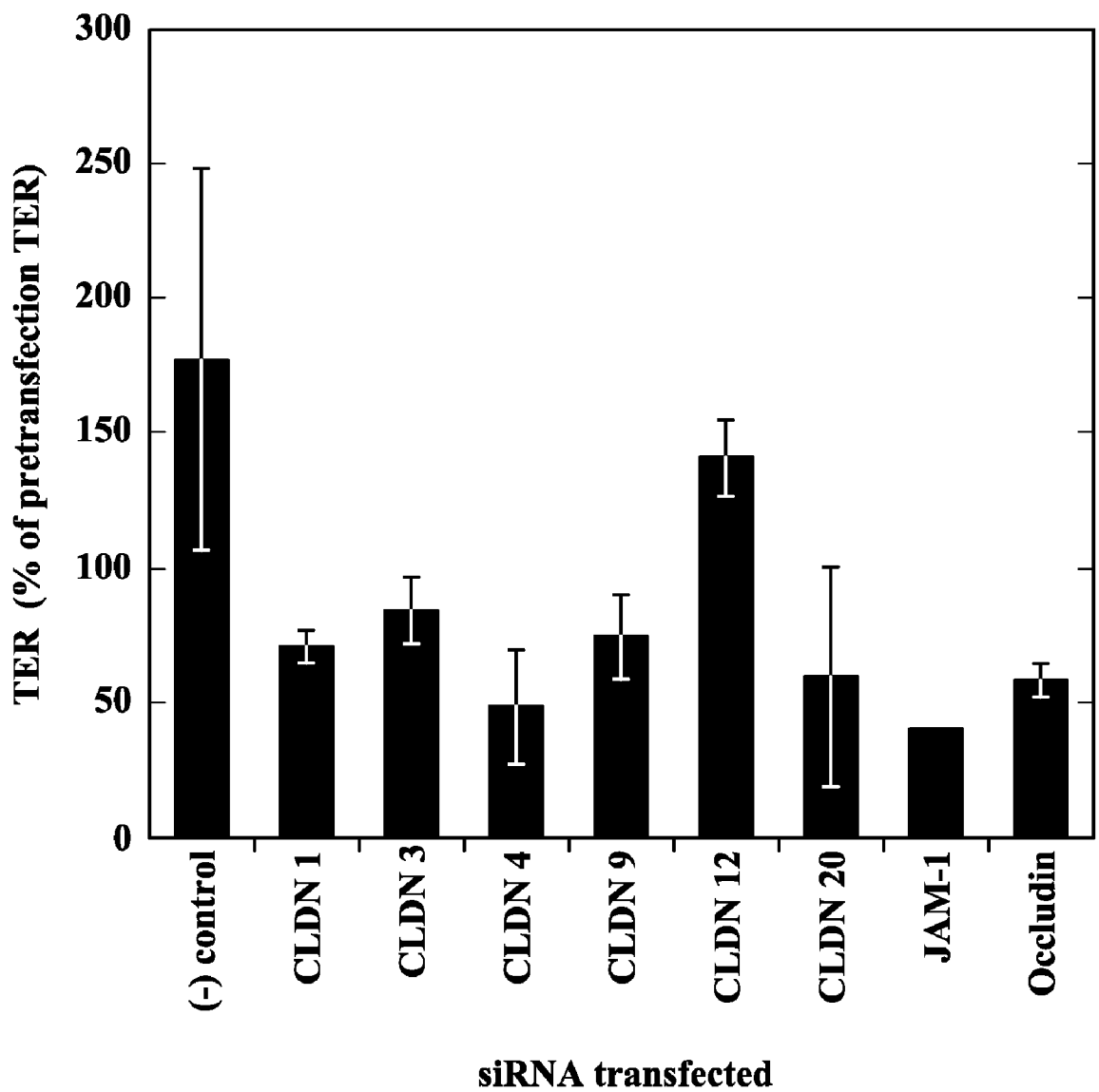
FIG. 3. Transfection of Selected siRNAs Against TJ Targets Decreases TER. 16HBE14 cells were grown on 12-well inserts for 3 days prior to transfection (80 μmol/insert). TER values measured at day 4 after transfection were near the optimal time point of TER recovery after transfection.
Figure 4A:
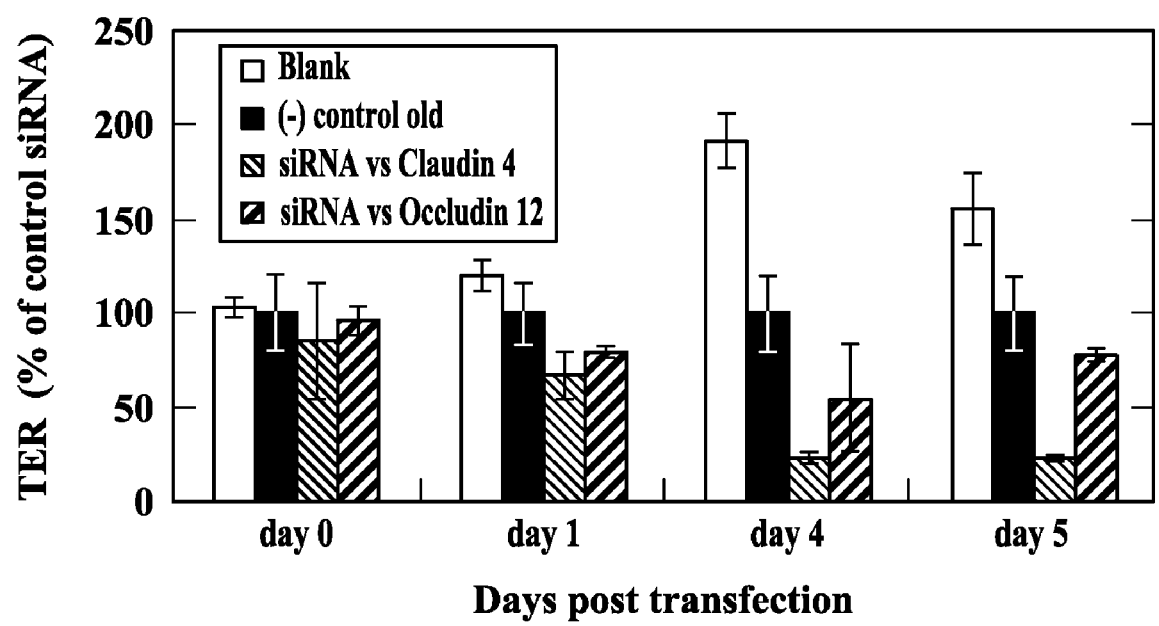
FIG. 4. CLDN 4 Knockdown Decreases TER. (A) Epithelial cells were grown on 12-well inserts to the stage where tight junctions formed as indicated by values for transepithelial electrical resistance (TER). siRNAs against claudins 4 and 12 and a negative control (80 μmol/each) were used individually to transfect cell monolayers. (B) Epithelial cells were grown in 6-well plates to 50% confluence followed by transfections with siRNA against claudin 4 and a negative control. TER values before day 9 are not shown since TER does not significantly develop until a mono-layer is established and tight junctions are formed.
Figure 4B:
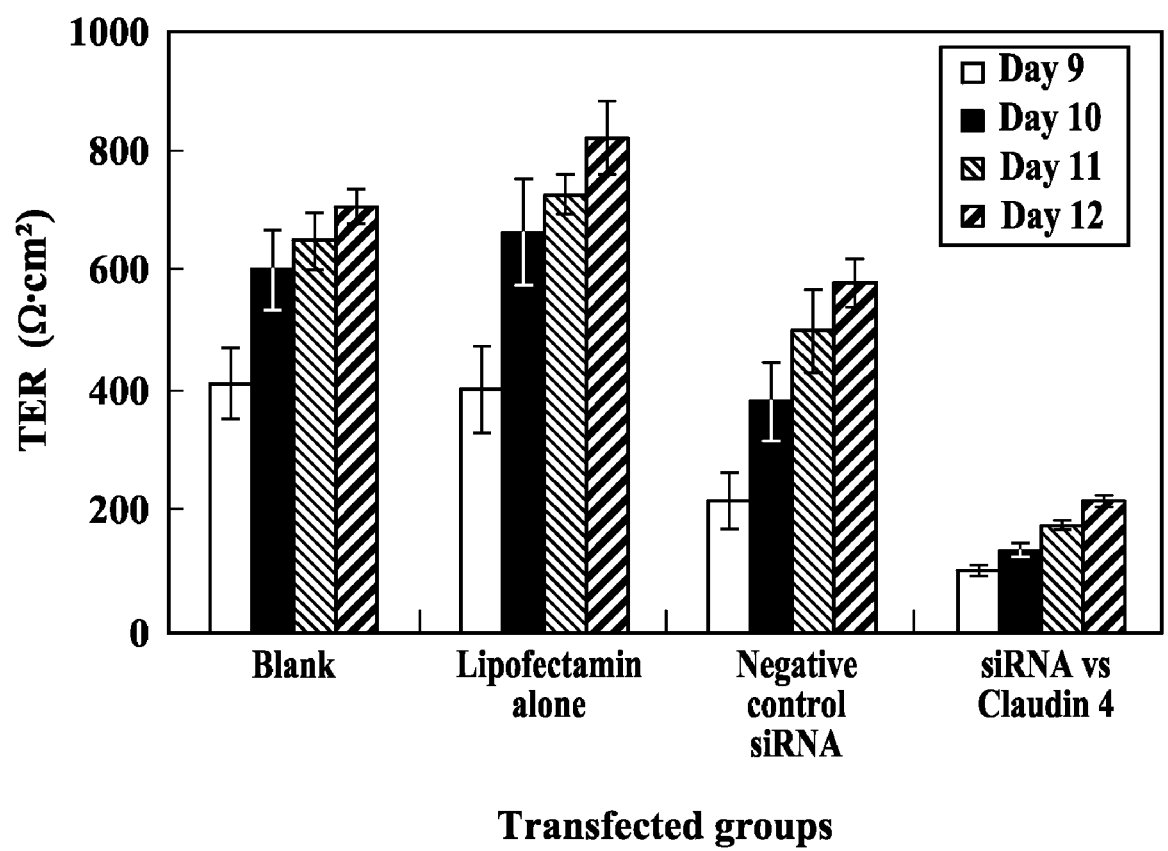
Figure 5:
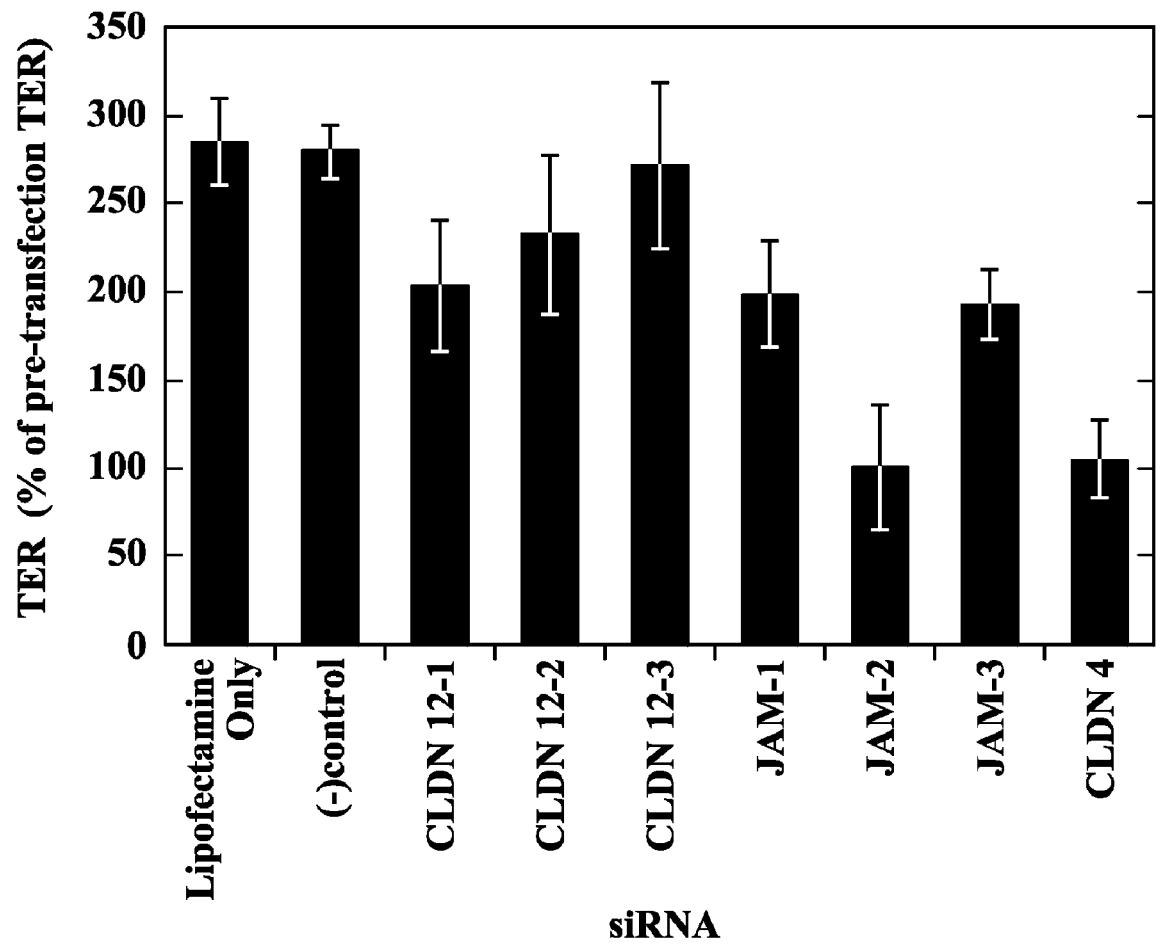
FIG. 5. Knockdown of Either CLDN 1 or 12 with CLDN 4 Decreases TER. Results indicate that ½ dose (40 μmol) did not show any significant effects on TER for any siRNA alone, while higher dose (80 μmol) of siRNA against CLDN 4 yields a knockdown effect. The effects of equal amounts of CLDN 4 and CLDN 1 (40 μmol each) is similar to 80-pmol of siRNA against CLDN 4 alone, while siRNA combinations with CLDN 12 (generally ineffective at any dose) have little effect.
Figure 6:
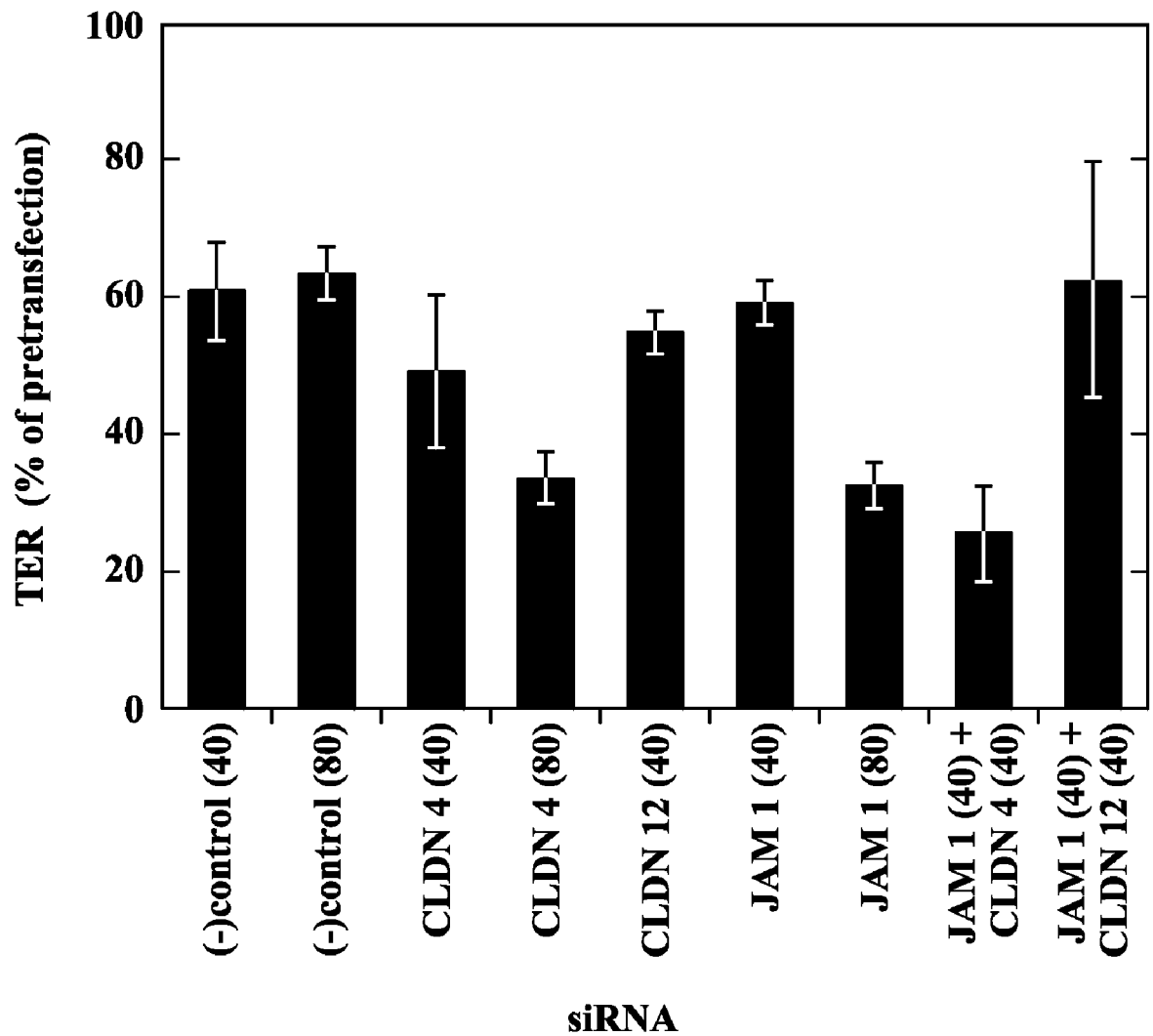
FIG. 6. Knockdown of Either CLDN 4 or 12 with JAM-1 Decreases TER. Results indicate that ½ dose (40 μmol) did not show any significant effects on TER for any siRNA alone, while higher dose (80 μmol) siRNA against CLDN 4 yields a knocking down effect. The effects of equal amount of CLDN 4 and JAM 1(40 μmol each) is similar with 80-pmol of siRNA against CLDN 4 alone, while pairing with siRNA against CLDN 12 (generally ineffective at any dose) has little effect.
Figure 7:
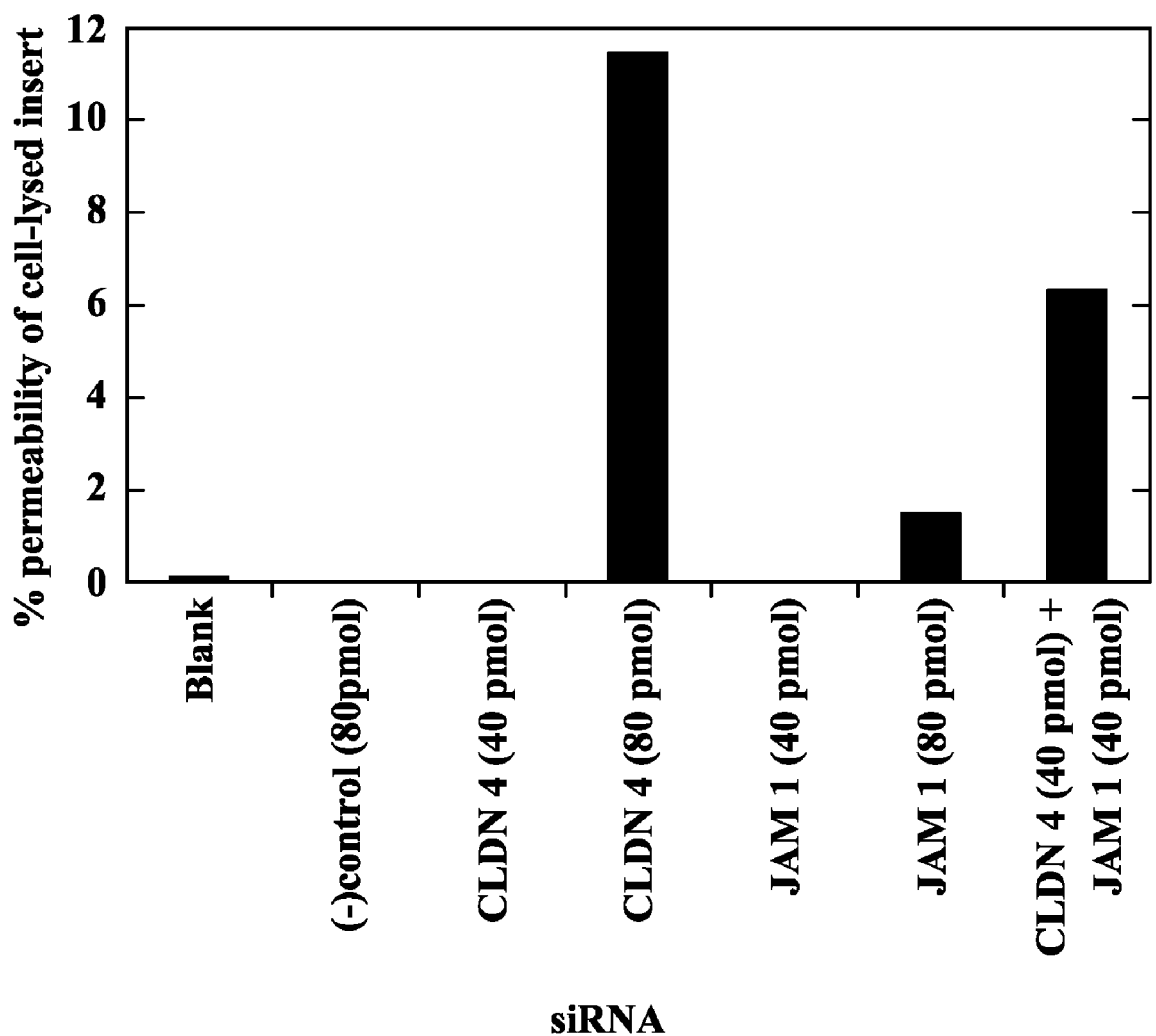
FIG. 7. Increased Dextran Permeability in siRNA Transfected Cells Correlates with Decreases in TER. Permeability assays were conducted on day 5 after transfection of 16HBE14o- Cell Inserts with siRNAs against indicated targets, using FITC-dextran, MW 4,400 in MEM/f12 media. The changes in permeability correlated well with changes in TER values (FIG. 6).
Figure 8:
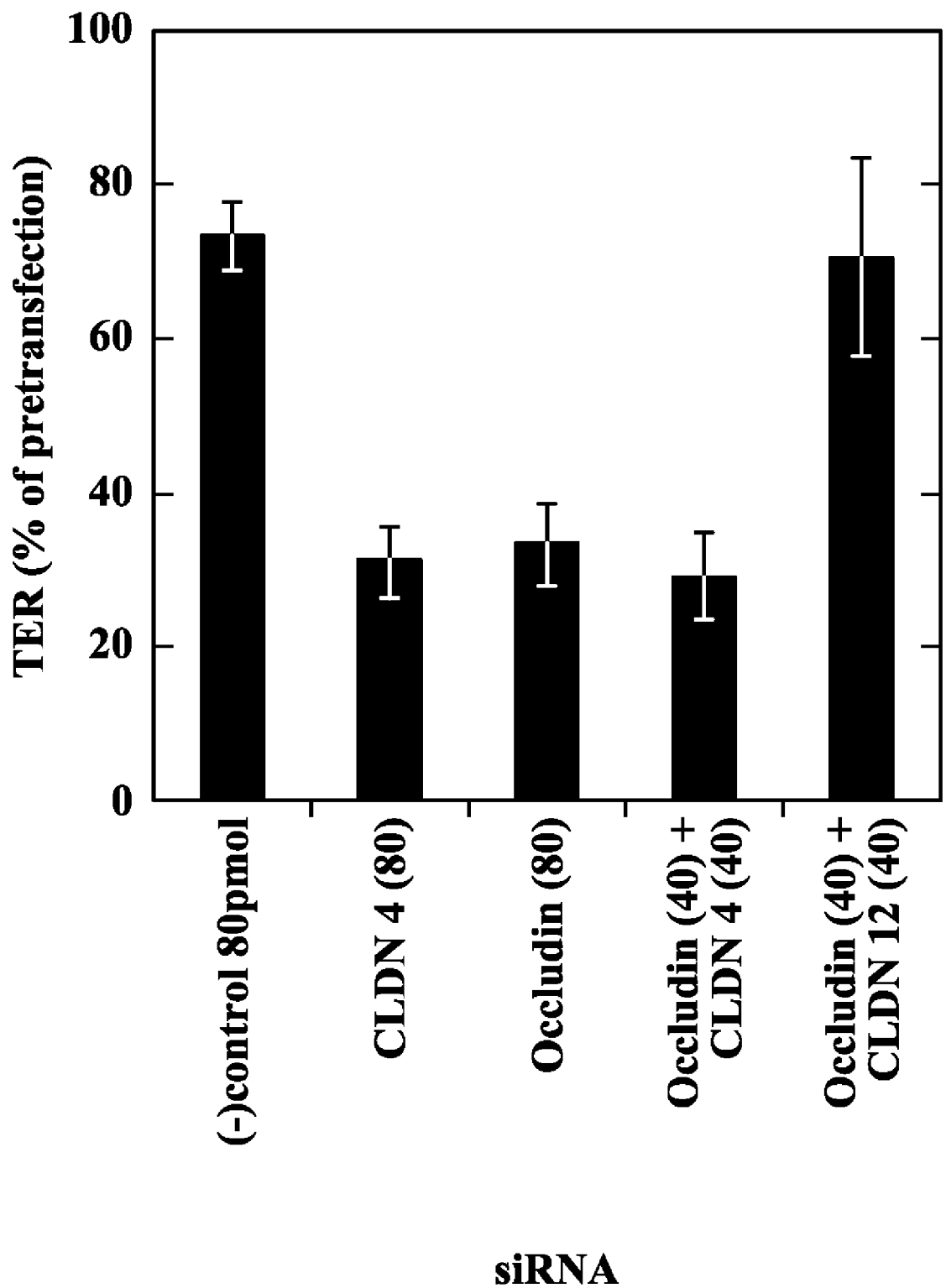
FIG. 8. Knockdown of Either CLDN 4 or 12 and Occludin Decreases TER. Results indicate that ½ dose (40 μmol) did not show any significant effects on TER for any siRNA alone (see FIGS. 5 and 6), while higher dose (80 μmol) siRNA against CLDN 4 yields a knockdown effect. The effects of equal amounts of CLDN 4 and occludin (40 μmol each) is similar to 80 μmol of siRNA against CLDN 4 alone, while combination with siRNA against CLDN 12 (generally ineffective at any dose) has little effect.

The instant invention satisfies the foregoing needs and fulfills additional objects and advantages by providing novel pharmaceutical compositions methods that open the tight-junctions in the nose. These compositions are antagonists to either the extracellular domain of the JAM-1 protein or the extracellular domain of the claudin-4 protein or the extracellular domain of the occludin protein. Examples of these are antibodies, antibody fragments and single chain antibodies that bind to either junctional adhesion molecule-1 (JAM-1), occludin or claudin-4. The permeabilizing agent reversibly enhances mucosal epithelial paracellular transport, typically by modulating epithelial junctional structure and/or physiology at a mucosal epithelial surface in the subject. This effect typically involves inhibition by the permeabilizing agent of homotypic or heterotypic binding between epithelial membrane adhesive proteins of neighboring epithelial cells. Also, small interfering nucleic acids can be used to downregulate the peptides through the mechanism of RNA interference as described below and thus open the tight junctions.

Epithelial cells provide a crucial interface between the external environment and mucosal and submucosal tissues and extracellular compartments. One of the most important functions of mucosal epithelial cells is to determine and regulate mucosal permeability. In this context, epithelial cells create selective permeability barriers between different physiological compartments. Selective permeability is the result of regulated transport of molecules through the cytoplasm (the transcellular pathway) and the regulated permeability of the spaces between the cells (the paracellular pathway).

Intercellular junctions between epithelial cells are known to be involved in both the maintenance and regulation of the epithelial barrier function, and cell-cell adhesion. The tight junction (TJ) of epithelial and endothelial cells is a particularly important cell-cell junction that regulates permeability of the paracellular pathway, and also divides the cell surface into apical and basolateral compartments. Tight junctions form continuous circumferential intercellular contacts between epithelial cells and create a regulated barrier to the paracellular movement of water, solutes, and immune cells. They also provide a second type of barrier that contributes to cell polarity by limiting exchange of membrane lipids between the apical and basolateral membrane domains.

Tight junctions are thought to be directly involved in barrier and fence functions of epithelial cells by creating an intercellular seal to generate a primary barrier against the diffusion of solutes through the paracellular pathway, and by acting as a boundary between the apical and basolateral plasma membrane domains to create and maintain cell polarity, respectively. Tight junctions are also implicated in the transmigration of leukocytes to reach inflammatory sites. In response to chemo-attractants, leukocytes emigrate from the blood by crossing the endothelium and, in the case of mucosal infections, cross the inflamed epithelium. Transmigration occurs primarily along the paracellular rout and appears to be regulated via opening and closing of tight junctions in a highly coordinated and reversible manner.

Numerous proteins have been identified in association with TJs, including both integral and peripheral plasma membrane proteins. Current understanding of the complex structure and interactive functions of these proteins remains limited. Among the many proteins associated with epithelial junctions, several categories of trans-epithelial membrane proteins have been identified that may function in the physiological regulation of epithelial junctions. These include a number of "junctional adhesion molecules" (JAMs) and other TJ-associated molecules designated as occludins, claudins, and zonulin.

JAMs, occludin, and claudin extend into the paracellular space, and these proteins in particular have been contemplated as candidates for creating an epithelial barrier between adjacent epithelial cells and channels through epithelial cell layers. In one model, occludin, claudin, and JAM have been proposed to interact as homophilic binding partners to create a regulated barrier to paracellular movement of water, solutes, and immune cells between epithelial cells.

A cDNA encoding murine junctional adhesion molecule-1 (JAM-1) has been cloned and corresponds to a predicted type I transmembrane protein (comprising a single transmembrane domain) with a molecular weight of approximately 32-kD, Williams, et al., *Molecular Immunology* 36:1175-1188, 1999; Gupta, et al., *IUBMB Life* 50:51-56, 2000; Ozaki, et al., *J. Immunol.* 163:553-557, 1999; Martin-Padura, et al., *J. Cell Biol.* 142:117-127, 1998. The extracellular segment of the molecule comprises two Ig-like domains described as an amino terminal "VH-type" and a carboxy-terminal "C2-type" carboxy-terminal β-sandwich fold, Bazzoni, et al., *Microcirculation* 8:143-152, 2001. Murine JAM-1 also contains two sites for N-glycosylation, and a cytoplasmic domain. The JAM-1 protein is a member of the immunoglobulin (Ig) superfamily and localizes to tight junctions of both epithelial and endothelial cells. Ultrastructural studies indicate that JAM-1 is limited to the membrane regions containing fibrils of occludin and claudin.

Transfection of a murine JAM-1-encoding cDNA into CHO cells leads to localization of the JAM-1 protein at cell-cell contacts, which only occurs in confluent monolayers when neighboring cells express JAM. In mixed cultures, where JAM transfectants are in contact with control transfectants, the protein remains diffuse—suggesting that JAM clustering is due to homophilic interaction, Martin-Padura, et al., *J. Cell Biol.* 142:117-127, 1998.

Experimental evidence suggests that JAM-1 can mediate homotypic adhesion and influence monocyte transmigration via heterotypic adhesive and de-adhesive interactions. A monoclonal antibody against murine JAM-1 inhibits transmigration of leukocytes across endothelial cells and in an in vivo model of skin inflammatory reaction, Martin-Padura, et al., *J. Cell Biol.* 142:117-127, 1998. Anti-murine JAM-1 antibodies also inhibit accumulation of leukocytes in the cerebrospinal fluid in cytokine-induced meningitis. It is unknown how these effects are mediated. In one model, the antibodies may inhibit a heterotypic interaction between JAM-1 and a leukocyte receptor, Del Maschio, et al., *J. Exp. Med.* 190:1351-1356, 1999. Alternatively, the anti-JAM-1 antibodies may stabilize a homophilic JAM-mediated interaction between neighboring cells and thereby inhibit dissociation of the junctional complex, Balda, et al., *Cell Devel. Biol.* 11:281-289, 2000.

One model for JAM-1 activity proposes that an extracellular domain of JAM-1 is involved in intercellular adhesive interactions. Formation of JAM-1 dimers is thought to be due to stable and noncovalent interactions. Dissociation of JAM-1 dimers into monomeric subunits is reported at high ionic strength and acidic pH. In this general model, JAM-1 dimers are hypothesized to act as building blocks for JAM-1-dependent homophilic adhesion. In particular, JAM-1 may dimerize in cis-interactions yielding parallel homodimers positioned at one cell surface, and the cis-dimerization might expose an interface available for homophilic adhesive interactions between JAM-1 molecules on opposing cell surfaces. This model could account for homotypic adhesion between adjoining cells within confluent endothelial or epithelial monolayers. In addition, JAM-1 dimers expressed on transmigrating leukocytes are proposed to interact with JAM-1 dimers expressed on endothelial cells, thus accounting for the adhesion and de-adhesion events that occur during leukocyte transendothelial migration, Dejana, et al., *Throb. Haemost.* 86:308-315, 2001.

The putative extracellular domain of human JAM-1 was recently expressed as a fusion protein to generate anti-human JAM-1 antibodies that inhibited transepithelial resistance recovery (TER) in T84 cell monolayers after tight junction disruption mediated by transient calcium depletion, Liu, et al., *J. Cell. Sci.* 113:2363-2374, 2000. In particular, the anti-JAM antibodies inhibit JAM-1 and occludin redistribution to TJs following calcium mediated disruption. However, these authors report that purified recombinant human JAM-1 containing the extracellular domain does not inhibit TER after tight junction disruption, contrary to published results for murine JAM-1. On this basis it is considered that the data may not support a model of extracellular homo- or heterotypic interaction mediated by the human JAM-1 extracellular domain. In another study investigating the structure/function of human JAM-1, Williams, et al., *Mol. Immunol.* 36:1175-1188, 1999, report that both murine and human JM Fc chimeras and transfected COS cells failed to show homotypic adhesion for the protein in vitro—suggesting that "firm adhesion may not be the function of this molecule in vivo." In a separate study, Liang, et al., *Am. J. Physiol.* 279:1733-1743, 2000 report that a recombinant soluble form of human JAM-1 inhibits recovery of TER following trypsin-EDTA disruption of TJs. The following shows the amino acid sequence of JAM-1 in which the extracellular domain is underlined.

Human JAM-1: 299 amino acids.
(SEQ ID NO: 1)
MGTKAQVERKLLCLFILAILLCSLALGSVTVHSSEPEVRIPENNPVKLSC

AYSGFSSPRVEWKFDQGDTTRLVCYNNKITASYEDRVTFLPTGITFKSVT

REDTGTYTCMVSEEGGNSYGEVKVKLIVLVPPSKPTVNIPSSATIGNRAV

LTCSEQDGSPPSEYTWFKDGIVMPTNPKSTRAFSNSSYVLNPTTGELVFD

PLSASDTGEYSCEARNGYGTPMTSNAVRMEAVERNVGVIVAAVLVTLILL

GILVFGIWFAYSRGHFDRTKKGTSSKKVIYSQPSARSEGEFKQTSSFLV

The following shows the amino acid sequence of claudin-4 in which the extracellular domain of the protein is underlined.

Human Claudin-4: 209 amino acids.
(SEQ ID NO: 2)
MASMGLQVMGIALAVLGWLAVMLCCALPMWRVTAFIGSNIVTSQTIWEGL

WMNCVVQSTGQMQCKVYDSLLALPQDLQAARALVIISIIVAALGVLLSVV

GGKCTNCLEDESAKAKTMIVAGVVFLLAGLMVIVPVSWTAHNIIQDFYNP

LVASGQKREMGASLYVGWAASGLLLLGGGLLCCNCPPRTDKPYSAKYSAA

RSAAASNYV

The following shows the amino acid sequence of human occludin in which the extracellular domain of the protein is underlined.

Human Occludin: 522 amino acids.
(SEQ ID NO: 56)
MSSRPLESPPPYRPDEFKPNHYAPSNDIYGGEMHVRPMLSQPAYSFYPED

EILHFYKWTSPPGVIRILSMLIIVMCIAIFACVASTLAWDRGYGTSLLGG

SVGYPYGGSGFGSYGSGYGYGYGYGYGGYTDPRAAKGFMLAMAAFCFI

AALVIFVTSVIRSEMSRTRRYYLSVIIVSAILGIMVFIATIVYIMGVNPT

AQSSGSLYGSQIYALCNQFYTPAATGLYVDQYLYHYCVVDPQEAIAIVLG

FMIIVAFALIIFFAVKTRRKMDRYDKSNILWDKEHIYDEQPPNVEEWVKN

VSAGTQDVPSPPSDYVERVDSPMAYSSNGKVNDKRFYPESSYKSTPVPEV

VQELPLTSPVDDFRQPRYSSGGNFETPSKRAPAKGRAGRSKRTEQDHYET

DYTTGGESCDELEEDWIREYPPITSDQQRQLYKRNFDTGLQEYKSLQSEL

DEINKELSRLDKELDDYREESEEYMAAADEYNRLKQVKGSADYKSKKNHC

KQLKSKLSHIKKMVGDYDRQKT

Thus, the invention also provides diagnostic and therapeutic antibodies, including monoclonal antibodies, directed against a JAM, occludin or claudin peptide or protein, including antibodies against specific portions or domains (e.g., a homotypic binding interface) of a JAM, occludin or claudin protein. The antibodies specifically recognize functional portions of the JAM, occludin or claudin protein, and are therefore useful for blocking interactions between these proteins, or permeabilizing mucosal epithelial target cells when administered in vivo. These immunotherapeutic reagents may include humanized antibodies, and can be combined for therapeutic use with additional active or inert ingredients as disclosed herein, e.g., in conventional pharmaceutically acceptable carriers or diluents, e.g., immunogenic adjuvants, and optionally with adjunctive or combinatorially active agents such as antiretroviral drugs. Methods for generating functional antibodies, including humanized antibodies, antibody fragments, and other related agents are well known in the art (see, e.g., Harlow & Lane, *Antibodies, A Laboratory Manual* (CSHP, NY, 1988); Queen, et al., *Proc. Natl. Acad. Sci. USA* 86:10029-10033, 1989, and WO 90/07861. Human antibodies can be obtained using phage-display methods (see, e.g., Dower, et al., WO 91/17271; McCafferty, et al., WO 92/01047). Similarly, methods for producing active antibody fragments are well known, including methods for generating separate heavy chains, light chains Fab, Fab'F(ab')$_2$, Fv, and single chain antibodies. Fragments can be produced by enzymatic or chemical separation of intact immunoglobulins using standard methods. Fab fragments may be obtained from F(ab')2 fragments by limited reduction, or from whole antibody by digestion with papain in the presence of reducing agents. Fragments can also be produced by recombinant DNA techniques. Segments of nucleic acids encoding selected fragments are produced by digestion of full-length coding sequences with restriction enzymes, or by de novo synthesis. Often fragments are expressed in the form of phage-coat fusion proteins. This manner of expression is advantageous for affinity-sharpening of antibodies.

According to the present invention, the tight junctions can also be opened using RNAi techniques. RNA interference refers to the process of sequence-specific post-transcriptional gene silencing in animals mediated by short interfering nucleic acids (siNAs), which are usually short interfering RNAs (siRNA). See Fire, et al., *Nature* 391:806, 1998, and Hamilton, et al., *Science* 286:950-951, 1999. The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla [Fire, et al., *Trends Genet.* 15:358, 1999]. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA. The presence of dsRNA in cells triggers the RNAi response though a mechanism that has yet to be fully characterized. This mechanism appears to be different from the interferon response that results from dsRNA-mediated activation of protein kinase PKR and 2',5'-oligoadenylate synthetase resulting in non-specific cleavage of mRNA by ribonuclease L.

The presence of long dsRNAs in cells stimulates the activity of a ribonuclease III enzyme referred to as dicer. Dicer is involved in the processing of the dsRNA into short pieces of dsRNA known as short interfering RNAs (siRNAs) [Hamilton, et al., supra; Berstein, et al., *Nature* 409:363, 2001]. Short interfering RNAs derived from dicer activity are typically about 21 to about 23 nucleotides in length and comprise about 19 base pair duplexes [Hamilton, et al., supra; Elbashir, et al., *Genes Dev.* 15:188, 2001]. The siRNA molecules bind to a protein complex termed RNA-induced silencing complex (RISC), which contains a helicase activity that unwinds the two strands of the siRNA molecules. RISC will then incorporate one strand into its complex, which strand will hybridize to a target mRNA and the RISC will hydrolyze or cleave the target mRNA at the site where the antisense strand is bound. Cleavage of the target RNA takes place in the middle of the region complementary to the antisense strand of the siRNA duplex [Elbashir, et al., *Genes Dev.* 15:188, 2001].

Elbashir, et al., *Nature* 411:494, 2001, describe RNAi induced by introduction of duplexes of synthetic 21-nucleotide RNAs in cultured mammalian cells including human embryonic kidney and HeLa cells. Recent work in Drosophila embryonic lysates [Elbashir, et al., *EMBO J.* 20:6877, 2001] has revealed certain requirements for siRNA length, structure, chemical composition, and sequence that are essential to mediate efficient RNAi activity. These studies have shown that 21-nucleotide siRNA duplexes are most active when containing 3'-terminal dinucleotide overhangs. Furthermore, complete substitution of one or both siRNA strands with 2'-deoxy (2'—H) or 2'—O-methyl nucleotides abolishes RNAi activity, whereas substitution of the 3'-terminal siRNA overhang nucleotides with 2'-deoxy nucleotides (2'—H) was shown to be tolerated. Single mismatch sequences in the center of the siRNA duplex were also shown to abolish RNAi activity. In addition, these studies also indicate that the position of the cleavage site in the target RNA is defined by the 5'-end of the siRNA guide sequence rather than the 3'-end of the guide sequence [Elbashir, et al., *EMBO J.* 20:6877, 2001]. Other studies have indicated that a 5'-phosphate on the target-complementary strand of a siRNA duplex is required for siRNA activity and that ATP is utilized to maintain the 5'-phosphate moiety on the siRNA [Nykanen, et al., *Cell* 107:309, 2001].

Nucleic acid molecules that act as mediators of the RNA interference gene silencing response are double-stranded nucleic acid molecules. The double-stranded nucleic acids are generally double-stranded RNA, however, the strands can contain one or more deoxyribonucleotides. The more precise term would be to call the RNAi mediators, small interfering nucleic acids or 'siNA.' The siNA molecules are comprised of duplexes containing about 19 base pairs between oligonucleotides comprising about 19 to about 25 (e.g., about 19, 20, 21, 22, 23, 24 or 25) nucleotides. The siNA molecules may also be comprised of duplexes with overhanging ends of about 1 to about 3 (e.g., about 1, 2, or 3) nucleotides, for example, about 21-nucleotide duplexes with about 19 base pairs and 3'-terminal mononucleotide, dinucleotide, or trinucleotide overhangs.

General Description of RNA Interference

The following is a further description of other general aspects and definitions relating to RNA interference Non-limiting examples of chemical modifications that can be made in an siNA include without limitation phosphorothioate internucleotide linkages, 2'-deoxyribonucleotides, 2'-O-methyl ribonucleotides, 2'-deoxy-2'-fluoro ribonucleotides, "universal base" nucleotides, "acyclic" nucleotides, 5-C-methyl nucleotides, and terminal glyceryl and/or inverted deoxy abasic residue incorporation. These chemical modifications, when used in various siNA constructs, are shown to preserve RNAi activity in cells while at the same time, dramatically increasing the serum stability of these compounds.

A composition comprising a siNA molecule may be in a pharmaceutically acceptable carrier or diluent.

In a non-limiting example, the introduction of chemically-modified nucleotides into nucleic acid molecules provides a powerful tool in overcoming potential limitations of in vivo stability and bioavailability inherent to native RNA molecules that are delivered exogenously. For example, the use of chemically-modified nucleic acid molecules can enable a lower dose of a particular nucleic acid molecule for a given therapeutic effect since chemically-modified nucleic acid molecules tend to have a longer half-life in serum. Furthermore, certain chemical modifications can improve the bioavailability of nucleic acid molecules by targeting particular cells or tissues and/or improving cellular uptake of the nucleic acid molecule. Therefore, even if the activity of a chemically-modified nucleic acid molecule is reduced as compared to a native nucleic acid molecule, for example, when compared to an all-RNA nucleic acid molecule, the overall activity of the modified nucleic acid molecule can be greater than that of the native molecule due to improved stability and/or delivery of the molecule. Unlike native unmodified siNA, chemically-modified siNA can also minimize the possibility of activating interferon activity in humans.

The siNA molecules described herein, the antisense region of a siNA molecule of the invention can comprise a phosphorothioate internucleotide linkage at the 3'-end of said antisense region. In any of the embodiments of siNA molecules described herein, the antisense region can comprise about one to about five phosphorothioate internucleotide linkages at the 5'-end of said antisense region. In any of the embodiments of siNA molecules described herein, the 3'-terminal nucleotide overhangs of a siNA molecule of the invention can comprise ribonucleotides or deoxyribonucleotides that are chemically-modified at a nucleic acid sugar, base, or backbone. In any of the embodiments of siNA molecules described herein, the 3'-terminal nucleotide overhangs can comprise one or more universal base ribonucleotides. In any of the embodiments of siNA molecules described herein, the 3'-terminal nucleotide overhangs can comprise one or more acyclic nucleotides.

For example, in a non-limiting example, the invention features a chemically-modified short interfering nucleic acid (siNA) having about 1, 2, 3, 4, 5, 6, 7, 8 or more phosphorothioate internucleotide linkages in one siNA strand. In yet another embodiment, the invention features a chemically-modified short interfering nucleic acid (siNA) individually having about 1, 2, 3, 4, 5, 6, 7, 8 or more phosphorothioate internucleotide linkages in both siNA strands. The phosphorothioate internucleotide linkages can be present in one or both oligonucleotide strands of the siNA duplex, for example in the sense strand, the antisense strand, or both strands. The siNA molecules of the invention can comprise one or more phosphorothioate internucleotide linkages at the 3'-end, the 5'-end, or both of the 3'-and 5'-ends of the sense strand, the antisense strand, or both strands. For example, an exemplary siNA molecule of the invention can comprise about 1 to about 5 or more (e.g., about 1, 2, 3, 4, 5, or more) consecutive phosphorothioate internucleotide linkages at the 5'-end of the sense strand, the antisense strand, or both strands. In another non-limiting example, an exemplary siNA molecule of the invention can comprise one or more (e.g., about 1, 2, 3, 4, 5, 6, 7, 8, 9, 10, or more) pyrimidine phosphorothioate internucleotide linkages in the sense strand, the antisense strand, or both strands. In yet another non-limiting example, an exemplary siNA molecule of the invention can comprise one or more (e.g., about 1, 2, 3, 4, 5, 6, 7, 8, 9, 10, or more) purine phosphorothioate internucleotide linkages in the sense strand, the antisense strand, or both strands.

An siNA molecule may be comprised of a circular nucleic acid molecule, wherein the siNA is about 38 to about 70 (e.g., about 38, 40, 45, 50, 55, 60, 65, or 70) nucleotides in length having about 18 to about 23 (e.g., about 18, 19, 20, 21, 22, or 23) base pairs wherein the circular oligonucleotide forms a dumbbell shaped structure having about 19 base pairs and 2 loops.

A circular siNA molecule contains two loop motifs, wherein one or both loop portions of the siNA molecule is biodegradable. For example, a circular siNA molecule of the invention is designed such that degradation of the loop portions of the siNA molecule in vivo can generate a double-stranded siNA molecule with 3'-terminal overhangs, such as 3'-terminal nucleotide overhangs comprising about 2 nucleotides.

Modified nucleotides present in siNA molecules, preferably in the antisense strand of the siNA molecules, but also optionally in the sense and/or both antisense and sense strands, comprise modified nucleotides having properties or characteristics similar to naturally occurring ribonucleotides. For example, the invention features siNA molecules including modified nucleotides having a Northern conformation (e.g., Northern pseudorotation cycle, see for example Saenger, *Principles of Nucleic Acid Structure*, Springer-Verlag ed., 1984). As such, chemically modified nucleotides present in the siNA molecules of the invention, preferably in the antisense strand of the siNA molecules of the invention, but also optionally in the sense and/or both antisense and sense strands, are resistant to nuclease degradation while at the same time maintaining the capacity to mediate RNAi. Non-limiting examples of nucleotides having a northern configuration include locked nucleic acid (LNA) nucleotides (e.g., 2'—O, 4'—C-methylene-(D-ribofuranosyl) nucleotides); 2'-methoxyethoxy (MOE) nucleotides; 2'-methyl-thio-ethyl, 2'-deoxy-2'-fluoro micleotides. 2'-deoxy-2'-chloro nucleotides, 2'-azido nucleotides, and 2'—O-methyl nucleotides.

The sense strand of a double stranded siNA molecule may have a terminal cap moiety such as an inverted deoxyabasic moiety, at the 3'-end, 5'-end, or both 3' and 5'-ends of the sense strand.

Non-limiting examples of conjugates include conjugates and ligands described in Vargeese, et al., U.S. patent application Ser. No. 10/427,160, filed Apr. 30, 2003, incorporated by reference herein in its entirety, including the drawings. In another embodiment, the conjugate is covalently attached to the chemically-modified siNA molecule via a biodegradable linker. In one embodiment, the conjugate molecule is attached at the 3'-end of either the sense strand, the antisense strand, or both strands of the chemically-modified siNA molecule. In another embodiment, the conjugate molecule is attached at the 5'-end of either the sense strand, the antisense strand, or both strands of the chemically-modified siNA molecule. In yet another embodiment, the conjugate molecule is attached both the 3'-end and 5'-end of either the sense strand, the antisense strand, or both strands of the chemically-modified siNA molecule, or any combination thereof. In one embodiment, a conjugate molecule of the invention comprises a molecule that facilitates delivery of a chemically-modified siNA molecule into a biological system, such as a cell. In another embodiment, the conjugate molecule attached to the chemically-modified siNA molecule is a poly ethylene glycol, human serum albumin, or a ligand for a cellular receptor that can mediate cellular uptake. Examples of specific conjugate molecules contemplated by the instant invention that can be attached to chemically-modified siNA molecules are described in Vargeese, et al., U.S. Patent Application Publication No. 20030130186, published Jul. 10, 2003, and U.S. Patent Application Publication No. 20040110296, published Jun. 10, 2004. The type of conjugates used and the extent of conjugation of siNA molecules of the invention can be evaluated for improved pharmacokinetic profiles, bioavailability, and/or stability of siNA constructs while at the same time maintaining the ability of the siNA to mediate RNAi activity. As such, one skilled in the art can screen siNA constructs that are modified with various conjugates to determine whether the siNA conjugate complex possesses improved properties while maintaining the ability to mediate RNAi, for example in animal models as are generally known in the art.

A siNA further may be further comprised of a nucleotide, non-nucleotide, or mixed nucleotide/non-nucleotide linker that joins the sense region of the siNA to the antisense region of the siNA. In one embodiment, a nucleotide linker can be a linker of >2 nucleotides in length, for example about 3, 4, 5, 6, 7, 8, 9, or 10 nucleotides in length. In another embodiment, the nucleotide linker can be a nucleic acid aptamer. By "aptamer" or "nucleic acid aptamer" as used herein is meant a nucleic acid molecule that binds specifically to a target molecule wherein the nucleic acid molecule has sequence that comprises a sequence recognized by the target molecule in its natural setting. Alternately, an aptamer can be a nucleic acid molecule that binds to a target molecule where the target molecule does not naturally bind to a nucleic acid. The target molecule can be any molecule of interest. For example, the aptamer can be used to bind to a ligand-binding domain of a protein, thereby preventing interaction of the naturally occurring ligand with the protein. This is a non-limiting example and those in the art will recognize that other embodiments can be readily generated using techniques generally known in the art. See, for example, Gold, et al., *Annu. Rev. Biochem.* 64:763, 1995; Brody and Gold, *J. Biotechnol.* 74:5, 2000; Sun, *Curr. Opin. Mol. Ther.* 2:100, 2000; Kusser, *J. Biotechnol.* 74:27, 2000; Hermann and Patel, *Science* 287:820, 2000; and Jayasena, *Clinical Chemistry* 45:1628, 1999.

A non-nucleotide linker may be comprised of an abasic nucleotide, polyether, polyamine, polyamide, peptide, carbohydrate, lipid, polyhydrocarbon, or other polymeric compounds (e.g., polyethylene glycols such as those having between 2 and 100 ethylene glycol units). Specific examples include those described by Seela and Kaiser, *Nucleic Acids Res.* 18:6353, 1990, and *Nucleic Acids Res.* 15:3113, 1987; Cload and Schepartz, *J. Am. Chem. Soc.* 113:6324, 1991; Richardson and Schepartz, *J. Am. Chem. Soc.* 113:5109, 1991; Ma, et al., *Nucleic Acids Res.* 21:2585, 1993, and *Biochemistry* 32:1751, 1993; Durand, et al., *Nucleic Acids Res.* 18:6353, 1990; McCurdy, et al., *Nucleosides & Nucleotides* 10:287, 1991; Jschke, et al., *Tetrahedron Lett.* 34:301, 1993; Ono, et al., *Biochemistry* 30:9914, 1991; Arnold, et al., International Publication No. WO 89/02439; Usman, et al., International Publication No. WO 95/06731; Dudycz, et al., International Publication No. WO 95/11910 and Ferentz and Verdine, *J. Am. Chem. Soc.* 113:4000, 1991. A "non-nucleotide" further means any group or compound that can be incorporated into a nucleic acid chain in the place of one or more nucleotide units, including either sugar and/or phosphate substitutions, and allows the remaining bases to exhibit their enzymatic activity. The group or compound can be abasic in that it does not contain a commonly recognized nucleotide base, such as adenosine, guanine, cytosine, uracil or thymine, for example at the C1 position of the sugar.

The synthesis of a siNA molecule of the invention, which can be chemically-modified, comprises: (a) synthesis of two complementary strands of the siNA molecule; (b) annealing the two complementary strands together under conditions suitable to obtain a double-stranded siNA molecule. In another embodiment, synthesis of the two complementary strands of the siNA molecule is by solid phase oligonucleotide synthesis. In yet another embodiment, synthesis of the two complementary strands of the siNA molecule is by solid phase tandem oligonucleotide synthesis.

Synthesis of Nucleic Acid Molecules

Oligonucleotides (e.g., certain modified oligonucleotides or portions of oligonucleotides lacking ribonucleotides) are synthesized using protocols known in the art, for example as described in Caruthers, et al., *Methods in Enzymology* 211, 3-19, 1992, Thompson, et al., International PCT Publication No. WO 99/54459, Wincott, et al., *Nucleic Acids Res.* 23:2677-2684, 1995; Wincott, et al., *Methods Mol. Bio.*, 74:59, 1997; Brennan, et al., *Biotechnol Bioeng.* 61:33-45, 1998; and Brennan, U.S. Pat. No. 6,001,311. RNA including certain siNA molecules of the invention follows the procedure as described in Usman, et al., *J. Am. Chem. Soc.* 109: 7845, 1987; Scaringe, et al., *Nucleic Acids Res.* 18:5433, 1990; and Wincott, et al., *Nucleic Acids Res.* 23:2677-2684, 1995; Wincott, et al., *Methods Mol. Bio.* 74:59, 1997.

Administration of Nucleic Acid Molecules

Methods for the delivery of nucleic acid molecules are described in Akhtar, et al., *Trends Cell Bio.* 2:139, 1992; Delivery Strategies for Antisense Oligonucleotide Therapeutics, ed. Akhtar, 1995, Maurer, et al., *Mol. Membr. Biol.* 16:129-140, 1999; Hofland and Huang, *Handb. Exp. Pharmacol.* 137:165-192, 1999; and Lee, et al., *ACS Symp. Ser.* 752:184-192, 2000, Sullivan, et al., PCT WO 94/02595, further describes the general methods for delivery of enzymatic nucleic acid molecules. These protocols can be utilized for the delivery of virtually any nucleic acid molecule. Nucleic acid molecules can be administered to cells by a variety of methods known to those of skill in the art, including, but not restricted to, encapsulation in liposomes, by iontophoresis, or by incorporation into other vehicles, such as hydrogels, cyclodextrins, biodegradable nanocapsules, and bioadhesive microspheres, or by proteinaceous vectors (O'Hare and Normand, International PCT Publication No. WO 00/53722). Alternatively, the nucleic acid/vehicle combination is locally delivered by direct injection or by use of an infusion pump. Direct injection of the nucleic acid molecules of the invention, whether subcutaneous, intramuscular, or intradermal, can take place using standard needle and syringe methodologies, or by needle-free technologies such as those described in Conry, et al., *Clin. Cancer Res.* 5:2330-2337, 1999, and Barry, et al., International PCT Publication No. WO 99/31262. The molecules of the instant invention can be used as pharmaceutical agents. Pharmaceutical agents prevent, modulate the occurrence, or treat (alleviate a symptom to some extent, preferably all of the symptoms) of a disease state in a patient.

Thus, the invention features a pharmaceutical composition comprising one or more nucleic acid(s) of the invention in an acceptable carrier, such as a stabilizer, buffer, and the like. The negatively charged polynucleotides of the invention can be administered (e.g., RNA, DNA or protein) and introduced into a patient by any standard means, with or without stabilizers, buffers, and the like, to form a pharmaceutical composition. When it is desired to use a liposome delivery mechanism, standard protocols for formation of liposomes can be followed. The compositions of the present invention may also be formulated and used as tablets, capsules or elixirs for oral administration, suppositories for rectal administration, sterile solutions, suspensions for injectable administration, and the other compositions known in the art.

The present invention also includes pharmaceutically acceptable formulations of the compounds described. These formulations include salts of the above compounds, e.g., acid addition salts, for example, salts of hydrochloric, hydrobromic, acetic acid, and benzene sulfonic acid.

A pharmacological composition or formulation refers to a composition or formulation in a form suitable for administration, e.g., systemic administration, into a cell or patient, including for example a human. Suitable forms, in part, depend upon the use or the route of entry, for example oral, transdermal, or by injection. Such forms should not prevent the composition or formulation from reaching a target cell (i.e., a cell to which the negatively charged nucleic acid is desirable for delivery). For example, pharmacological compositions injected into the blood stream should be soluble. Other factors are known in the art, and include considerations such as toxicity and forms that prevent the composition or formulation from exerting its effect.

By "systemic administration" is meant in vivo systemic absorption or accumulation of drugs in the blood stream followed by distribution throughout the entire body. Administration routes which lead to systemic absorption include, without limitation: intravenous, subcutaneous, intraperitoneal, inhalation, oral, intrapulmonary and intramuscular. Each of these administration routes expose the desired negatively charged polymers, e.g., nucleic acids, to an accessible diseased tissue. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation that can facilitate the association of drug with the surface of cells, such as, lymphocytes and macrophages is also useful. This approach may provide enhanced delivery of the drug to target cells by taking advantage of the specificity of macrophage and lymphocyte immune recognition of abnormal cells, such as cancer cells.

By "pharmaceutically acceptable formulation" is meant, a composition or formulation that allows for the effective distribution of the nucleic acid molecules of the instant invention in the physical location most suitable for their desired activity. Nonlimiting examples of agents suitable for formulation with the nucleic acid molecules of the instant invention include: P-glycoprotein inhibitors (such as Pluronic P85), which can enhance entry of drugs into the CNS [Jolliet-Riant and Tillement, *Fundam. Clin. Pharmacol.* 13:16-26, 1999]; biodegradable polymers, such as poly (DL-lactide-coglycolide) microspheres for sustained release delivery after intracerebral implantation (Emerich, D. F., et al., *Cell Transplant* 8:47-58, 1999] (Alkermes, Inc. Cambridge, Mass.); and loaded nanoparticles, such as those made of polybutylcyanoacrylate, which can deliver drugs across the blood brain barrier and can alter neuronal uptake mechanisms (*Prog Neuropsychopharmacol Biol Psychiatry* 23:941-949, 1999]. Other non-limiting examples of delivery strategies for the nucleic acid molecules of the instant invention include material described in Boado, et al., *J. Pharm. Sci.*, 87:1308-1315, 1998; Tyler, et al., *FEBS Lett.* 421:280-284, 1999; Pardridge, et al., *PNAS USA.* 92:5592-5596, 1995; Boado, *Adv. Drug Delivery Rev.* 15:73-107, 1995; Aldrian-Herrada, et al., *Nucleic Acids Res.* 26:4910-4916, 1998; and Tyler, et al., *PNAS USA.* 96:7053-7058, 1999.

The present invention also includes compositions prepared for storage or administration, which include a pharmaceutically effective amount of the desired compounds in a pharmaceutically acceptable carrier or diluent. Acceptable carriers or diluents for therapeutic use are well known in the pharmaceutical art, and are described, for example, in *Remington's Pharmaceutical Sciences*, Mack Publishing Co., A. R. Gennaro ed. 1985. For example, preservatives, stabilizers, dyes and flavoring agents may be provided. These include sodium benzoate, sorbic acid and esters of p-hydroxybenzoic acid. In addition, antioxidants and suspending agents may be used.

A pharmaceutically effective dose is that dose required to prevent, inhibit the occurrence of, or treat (alleviate a symptom to some extent, preferably all of the symptoms) a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.1 mg/kg and 100 mg/kg body weight/day of active ingredients is administered dependent upon potency of the negatively charged polymer.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono-or diglycerides. In addition, fatty acids such as oleic acid find use in the preparation of injectables.

The siNAs can also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

The siNAs can be modified extensively to enhance stability by modification with nuclease resistant groups, for example, 2'-amino, 2'—C-allyl, 2'-fluoro, 2'—O-methyl, 2'—H. For a review see Usman and Cedergren, TIBS 17:34, 1992; Usman, et al., Nucleic Acids Symp. Ser. 31:163, 1994. SiNA constructs can be purified by gel electrophoresis using general methods or can be purified by high pressure liquid chromatography and re-suspended in water.

Chemically synthesizing nucleic acid molecules with modifications (base, sugar and/or phosphate) can prevent their degradation by serum ribonucleases, which can increase their potency. See e.g., Eckstein, et al., International Publication No. WO 92/07065; Perrault, et al., Nature 344:565, 1990; Pieken, et al., Science 253:314, 1991; Usman and Cedergren, Trends in Biochem. Sci. 17:334, 1992; Usman, et al., International Publication No. WO 93/15187; and Rossi, et al., International Publication No. WO 91/03162; Sproat, U.S. Pat. No. 5,334,711; Gold, et al., U.S. Pat. No. 6,300,074. All of the above references describe various chemical modifications that can be made to the base, phosphate and/or sugar moieties of the nucleic acid molecules described herein.

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'—C-allyl, 2'-fluoro, 2'—O-methyl, 2'—O-allyl, 2'—H, nucleotide base modifications. For a review see Usman and Cedergren, TIBS 17:34, 1992; Usman, et al., Nucleic Acids Symp. Ser. 31:163, 1994; Burgin, et al., Biochemistry 35:14090, 1996. Sugar modification of nucleic acid molecules have been extensively described in the art. See Eckstein, et al., International Publication PCT No. WO 92/07065; Perrault, et al., Nature 344:565-568, 1990; Pieken, et al., Science 253:314-317, 1991; Usman and Cedergren, Trends in Biochem. Sci. 17:334-339, 1992; Usman, et al., International Publication PCT No. WO 93/15187; Sproat, U.S. Pat. No. 5,334,711 and Beigelman, et al., J. Biol. Chem. 270:25702, 1995; Beigelman et al., International PCT publication No. WO 97/26270; Beigelman, et al., U.S. Pat. No. 5,716,824; Usman, et al., U.S. Pat. No. 5,627,053; Woolf, et al., International PCT Publication No. WO 98/13526; Thompson, et al., Karpeisky, et al., Tetrahedron Lett. 39:1131, 1998; Earnshaw and Gait, Biopolymers (Nucleic Acid Sciences) 48:39-55, 1998; Verma and Eckstein, Annu. Rev. Biochem. 67:99-134, 1998; and Burlina, et al., Bioorg. Med. Chem. 5:1999-2010, 1997. Such publications describe general methods and strategies to determine the location of incorporation of sugar, base and/or phosphate modifications and the like into nucleic acid molecules without modulating catalysis. In view of such teachings, similar modifications can be used as described herein to modify the siNA nucleic acid molecules of the instant invention so long as the ability of siNA to promote RNAi in cells is not significantly inhibited.

While chemical modification of oligonucleotide internucleotide linkages with phosphorothioate, phosphorodithioate, and/or 5'-methylphosphonate linkages improves stability, excessive modifications can cause some toxicity or decreased activity. Therefore, when designing nucleic acid molecules, the amount of these internucleotide linkages should be minimized. The reduction in the concentration of these linkages should lower toxicity, resulting in increased efficacy and higher specificity of these molecules.

In one embodiment, the invention features modified siNA molecules, with phosphate backbone modifications comprising one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications, see Hunziker and Leumann, Nucleic Acid Analogues: Synthesis and Properties, in Modern Synthetic Methods, VCH, 1995, pp. 331-417, and Mesmaeker, et al., Novel Backbone Replacements for Oligonucleotides, in Carbohydrate Modifications in Antisense Research, ACS, 1994, pp. 24-39.

Methods for the delivery of nucleic acid molecules are described in Akhtar, et al., Trends Cell Bio., 2:139, 1992; Delivery Strategies for Antisense Oligonucleotide Therapeutics, ed. Akhtar, 1995; Maurer, et al., Mol. Membr. Biol. 16:129-140, 1999; Hofland and Huang, Handb. Exp. Pharmacol. 137:165-192, 1999; and Lee, et al., ACS Symp. Ser. 752:184-192, 2000. Beigelman, et al., U.S. Pat. No. 6,395,713 and Sullivan, et al., PCT WO 94/02595 further describe the general methods for delivery of nucleic acid molecules. These protocols can be utilized for the delivery of virtually any nucleic acid molecule. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see for example Gonzalez, et al., Bioconjugate Chem. 10:1068-1074, 1999; Wang, et al., International PCT Publication Nos. WO 03/47518 and WO 03/46185), poly (lacetic-co-glycolic)acid (PLGA) and PLCA microspheres (see for example, U.S. Pat. No. 6,447,796 and U.S. Patent Application Publication No. US 2002130430), biodegradable nanocapsules, and bioadhesive microspheres, or by proteinaceous vectors (O'Hare and Normand, International PCT Publication No. WO 00/53722). Alternatively, the nucleic acid/vehicle combination is locally delivered by direct injection or by use of an infusion pump. Direct injection of the nucleic acid molecules of the invention, whether subcutaneous, intramuscular, or intradermal, can take place using standard needle and syringe methodologies, or by needle-free technologies such as those described in Conry, et al., Clin. Cancer Res. 5:2330-2337, 1999, and Barry, et al., International PCT Publication No. WO 99/31262. The molecules of the instant invention can be used as pharmaceutical agents. Pharmaceutical agents prevent, modulate the occurrence, or treat (alleviate a symptom to some extent, preferably all of the symptoms) of a disease state in a subject.

The term "short interfering nucleic acid", "siNA", "short interfering RNA", "siRNA", "short interfering nucleic acid molecule", "short interfering oligonucleotide molecule", or "chemically-modified short interfering nucleic acid molecule" as used herein refers to any nucleic acid molecule capable of inhibiting or down regulating gene expression or viral replication, for example by mediating RNA interference "RNAi" or gene silencing in a sequence-specific manner. For example the siNA can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The siNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure, for example wherein the double stranded region is about 19 base pairs); the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof. Alternatively, the siNA is assembled from a single oligonucleotide, where the self-complementary sense and antisense regions of the siNA are linked by means of a nucleic acid based or non-nucleic acid-based linker(s). The siNA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The siNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (for example, where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez, et al., Cell 110:563-574, 2002, and Schwarz, et al., Molecular Cell 10:537-568, 2002, or 5',3'-diphosphate. In certain embodiments, the siNA molecule of the invention comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, Van der Waals interactions, hydrophobic interactions, and/or stacking interactions. In certain embodiments, the siNA molecules of the invention comprise nucleotide sequence that is complementary to nucleotide sequence of a target gene. In another embodiment, the siNA molecule of the invention interacts with nucleotide sequence of a target gene in a manner that causes inhibition of expression of the target gene. As used herein, siNA molecules need not be limited to those molecules containing only RNA, but further encompasses chemically-modified nucleotides and non-nucleotides. In certain embodiments, the short interfering nucleic acid molecules of the invention lack 2'-hydroxy (2'—OH) containing nucleotides. In certain embodiments short interfering nucleic acids do not require the presence of nucleotides having a 2'-hydroxy group for mediating RNAi and as such, short interfering nucleic acid molecules of the invention optionally do not include any ribonucleotides (e.g., nucleotides having a 2'—OH group). Such siNA molecules that do not require the presence of ribonucleotides within the siNA molecule to support RNAi can however have an attached linker or linkers or other attached or associated groups, moieties, or chains containing one or more nucleotides with 2'—OH groups. Optionally, siNA molecules can comprise ribonucleotides at about 5, 10, 20, 30, 40, or 50% of the nucleotide positions. As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (mRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, siNA molecules of the invention can be used to epigenetically silence genes at both the post-transcriptional level or the pre-transcriptional level. In a non-limiting example, epigenetic regulation of gene expression by siNA molecules of the invention can result from siNA mediated modification of chromatin structure to alter gene expression. See, for example, Allshire, Science 297:1818-1819, 2002; Volpe, et al., Science 297: 1833-1837, 2002; Jenuwein, Science 297:2215-2218, 2002; and Hall, et al., Science 297:2232-2237, 2002.

By "asymmetric hairpin" as used herein is meant a linear siNA molecule comprising an antisense region, a loop portion that can comprise nucleotides or non-nucleotides, and a sense region that comprises fewer nucleotides than the antisense region to the extent that the sense region has enough complementary nucleotides to base pair with the antisense region and form a duplex with loop. For example, an asymmetric hairpin siNA molecule of the invention can comprise an antisense region having length sufficient to mediate RNAi in a T-cell (e.g., about 19 to about 22 (e.g., about 19, 20, 21, or 22) nucleotides) and a loop region comprising about 4 to about 8 (e.g., about 4, 5, 6, 7, or 8) nucleotides, and a sense region having about 3 to about 18 (e.g., about 3, 4, 5, 6, 7, 8, 9, 10, 11, 12, 13, 14, 15, 16, 17, or 18) nucleotides that are complementary to the antisense region. The asymmetric hairpin siNA molecule can also comprise a 5'-terminal phosphate group that can be chemically modified. The loop portion of the asymmetric hairpin siNA molecule can comprise nucleotides, non-nucleotides, linker molecules, or conjugate molecules as described herein.

By "asymmetric duplex" as used herein is meant a siNA molecule having two separate strands comprising a sense region and an antisense region, wherein the sense region comprises fewer nucleotides than the antisense region to the extent that the sense region has enough complementary nucleotides to base pair with the antisense region and form a duplex. For example, an asymmetric duplex siNA molecule of the invention can comprise an antisense region having length sufficient to mediate RNAi in a T-cell (e.g., about 19 to about 22 (e.g., about 19, 20, 21, or 22) nucleotides) and a sense region having about 3 to about 18 (e.g., about 3, 4, 5, 6, 7, 8, 9, 10, 11, 12, 13, 14, 15, 16, 17, or 18) nucleotides that are complementary to the antisense region.

By "modulate" is meant that the expression of the gene, or level of RNA molecule or equivalent RNA molecules encoding one or more proteins or protein subunits, or activity of one or more proteins or protein subunits is up regulated or down regulated, such that expression, level, or activity is greater than or less than that observed in the absence of the modulator. For example, the term "modulate" can mean "inhibit," but the use of the word "modulate" is not limited to this definition.

By "inhibit", "down-regulate", or "reduce", it is meant that the expression of the gene, or level of RNA molecules or equivalent RNA molecules encoding one or more proteins or protein subunits, or activity of one or more proteins or protein subunits, is reduced below that observed in the absence of the nucleic acid molecules (e.g., siNA) of the invention. In one embodiment, inhibition, down-regulation or reduction with an siNA molecule is below that level observed in the presence of an inactive or attenuated molecule. In another embodiment, inhibition, down-regulation, or reduction with siNA molecules is below that level observed in the presence of, for example, an siNA molecule with scrambled sequence or with mismatches. In another embodiment, inhibition, down-regulation, or reduction of gene expression with a nucleic acid molecule of the instant invention is greater in the presence of the nucleic acid molecule than in its absence.

By "highly conserved sequence region" is meant, a nucleotide sequence of one or more regions in a target gene does not vary significantly from one generation to the other or from one biological system to the other.

By "sense region" is meant a nucleotide sequence of a siNA molecule having complementarity to an antisense region of the siNA molecule. In addition, the sense region of a siNA molecule can comprise a nucleic acid sequence having homology with a target nucleic acid sequence.

By "antisense region" is meant a nucleotide sequence of a siNA molecule having complementarity to a target nucleic acid sequence. In addition, the antisense region of a siNA molecule can optionally comprise a nucleic acid sequence having complementarity to a sense region of the siNA molecule.

By "target nucleic acid" is meant any nucleic acid sequence whose expression or activity is to be modulated. The target nucleic acid can be DNA or RNA.

By "complementarity" is meant that a nucleic acid can form hydrogen bond(s) with another nucleic acid sequence by either traditional Watson-Crick or other non-traditional types. In reference to the nucleic molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art [see, e.g., Turner, et al., *CSH Symp. Quant. Biol.*, LII, pp. 123-133, 1987; Frier, et al., *Proc. Nat. Acad. Sci. USA* 83:9373-9377, 1986; Turner, et al., *J. Am. Chem. Soc.* 109:3783-3785, 1987]. A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, or 10 nucleotides out of a total of 10 nucleotides in the first oligonucleotide being based paired to a second nucleic acid sequence having 10 nucleotides represents 50%, 60%, 70%, 80%, 90%, and 100% complementary respectively). "Perfectly complementary" means that all the contiguous residues of a nucleic acid sequence will hydrogen bond with the same number of contiguous residues in a second nucleic acid sequence.

As used herein "cell" is used in its usual biological sense, and does not refer to an entire multicellular organism, e.g., specifically does not refer to a human. The cell can be present in an organism, e.g., birds, plants and mammals such as humans, cows, sheep, apes, monkeys, swine, dogs, and cats. The cell can be prokaryotic (e.g., bacterial cell) or eukaryotic (e.g., mammalian or plant cell). The cell can be of somatic or germ line origin, totipotent or pluripotent, dividing or non-dividing. The cell can also be derived from or can comprise a gamete or embryo, a stem cell, or a fully differentiated cell.

By "vectors" is meant any nucleic acid- and/or viral-based technique used to deliver a desired nucleic acid.

By "comprising" is meant including, but not limited to, whatever follows the word "comprising." Thus, use of the term "comprising" indicates that the listed elements are required or mandatory, but that other elements are optional and may or may not be present. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

By "RNA" is meant a molecule comprising at least one ribonucleotide residue. By "ribonucleotide" is meant a nucleotide with a hydroxyl group at the 2' position of a .beta.-D-ribo-furanose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

By "subject" is meant an organism, which is a donor or recipient of explanted cells or the cells themselves. "Subject" also refers to an organism to which the nucleic acid molecules of the invention can be administered. A subject can be a mammal or mammalian cells, including a human or human cells.

The term "universal base" as used herein refers to nucleotide base analogs that form base pairs with each of the natural DNA/RNA bases with little discrimination between them. Non-limiting examples of universal bases include C-phenyl, C-naphthyl and other aromatic derivatives, inosine, azole carboxamides, and nitroazole derivatives such as 3-nitropyrrole, 4-nitroindole, 5-nitroindole, and 6-nitroindole as known in the art [see for example, Loakes, *Nucleic Acids Research* 29:2437-2447, 2001].

The term "acyclic nucleotide" as used herein refers to any nucleotide having an acyclic ribose sugar, for example where any of the ribose carbons (C1, C2, C3, C4, or C5), are independently or in combination absent from the nucleotide.

The term "biodegradable" as used herein, refers to degradation in a biological system, for example enzymatic degradation or chemical degradation.

The term "biologically active molecule" as used herein, refers to compounds or molecules that are capable of eliciting or modifying a biological response in a system. Non-limiting examples of biologically active siNA molecules either alone or in combination with other molecules contemplated by the instant invention include therapeutically active molecules such as antibodies, cholesterol, hormones, antivirals, peptides, proteins, chemotherapeutics, small molecules, vitamins, co-factors, nucleosides, nucleotides, oligonucleotides, enzymatic nucleic acids, antisense nucleic acids, triplex forming oligonucleotides, 2,5-A chimeras, siNA, dsRNA, allozymes, aptamers, decoys and analogs thereof. Biologically active molecules of the invention also include molecules capable of modulating the pharmacokinetics and/or pharmacodynamics of other biologically active molecules, for example, lipids and polymers such as polyamines, polyamides, polyethylene glycol and other polyethers.

The term "phospholipid" as used herein, refers to a hydrophobic molecule comprising at least one phosphorus group. For example, a phospholipid can comprise a phosphorus-containing group and saturated or unsaturated alkyl group, optionally substituted with OH, COOH, oxo, amine, or substituted or unsubstituted aryl groups.

By "cap structure" is meant chemical modifications, which have been incorporated at either terminus of the oligonucleotide (see, for example, Adamic, et al., U.S. Pat. No. No. 5,998,203). These terminal modifications protect the nucleic acid molecule from exonuclease degradation, and may help in delivery and/or localization within a cell. The cap may be present at the 5'-terminus (5'-cap) or at the 3'-terminal (3'-cap) or may be present on both termini. In non-limiting examples, the 5'-cap includes, but is not limited to, glyceryl, inverted deoxy abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety.

Non-limiting examples of the 3'-cap include, but are not limited to, glyceryl, inverted deoxy abasic residue (moiety), 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Lyer, *Tetrahedron* 49:1925, 1993; incorporated by reference herein).

By the term "non-nucleotide" is meant any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenosine, guanine, cytosine, uracil or thymine and therefore lacks a base at the 1'-position.

By "nucleotide" as used herein is as recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety (also referred to interchangeably as nucleotide analogs, modified nucleotides, non-natural nucleotides, non-standard nucleotides and other; see, for example, Usman and McSwiggen, supra; Eckstein, et al., International PCT Publication No. WO 92/07065; Usman, et al., International PCT Publication No. WO 93/15187; Uhlman & Peyman, supra). There are several examples of modified nucleic acid bases known in the art as summarized by Limbach, et al., *Nucleic Acids Res.* 22:2183, 1994. Some of the non-limiting examples of base modifications that can be introduced into nucleic acid molecules include, inosine, purine, pyridin-4-one, pyridin-2-one, phenyl, pseudouracil, 2, 4, 6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g., 6-methyluridine), propyne, and others (Burgin, et al., *Biochemistry* 35:14090, 1996; Uhlman & Peyman, supra). By "modified bases" in this aspect is meant nucleotide bases other than adenine, guanine, cytosine and uracil at 1' position or their equivalents.

By "target site" is meant a sequence within a target RNA that is "targeted" for cleavage mediated by a siNA construct which contains sequences within its antisense region that are complementary to the target sequence.

By "detectable level of cleavage" is meant cleavage of target RNA (and formation of cleaved product RNAs) to an extent sufficient to discern cleavage products above the background of RNAs produced by random degradation of the target RNA. Production of cleavage products from 1-5% of the target RNA is sufficient to detect above the background for most methods of detection.

By "biological system" is meant, material, in a purified or unpurified form, from biological sources, including but not limited to human, animal, plant, insect, bacterial, viral or other sources, wherein the system comprises the components required for RNAi activity. The term "biological system" includes, for example, a cell, tissue, or organism, or extract thereof. The term biological system also includes reconstituted RNAi systems that can be used in an in vitro setting.

The term "biodegradable linker" as used herein, refers to a nucleic acid or non-nucleic acid linker molecule that is designed as a biodegradable linker to connect one molecule to another molecule, for example, a biologically active molecule to a siNA molecule of the invention or the sense and antisense strands of a siNA molecule of the invention. The biodegradable linker is designed such that its stability can be modulated for a particular purpose, such as delivery to a particular tissue or cell type. The stability of a nucleic acid-based biodegradable linker molecule can be modulated by using various chemistries, for example combinations of ribonucleotides, deoxyribonucleotides, and chemically-modified nucleotides, such as 2'—O-methyl, 2'-fluoro, 2'-amino, 2'—O-amino, 2'—C-allyl, 2'—O-allyl, and other 2'-modified or base modified nucleotides. The biodegradable nucleic acid linker molecule can be a dimer, trimer, tetramer or longer nucleic acid molecule, for example, an oligonucleotide of about 2, 3, 4, 5, 6, 7, 8, 9, 10, 11, 12, 13, 14, 15, 16, 17, 18, 19, or nucleotides in length, or can comprise a single nucleotide with a phosphorus-based linkage, for example, a phosphoramidate or phosphodiester linkage. The biodegradable nucleic acid linker molecule can also comprise nucleic acid backbone, nucleic acid sugar, or nucleic acid base modifications.

By "abasic" is meant sugar moieties lacking a base or having other chemical groups in place of a base at the 1' position, see for example Adamic, et al., U.S. Pat. No. 5,998,203.

By "unmodified nucleoside" is meant one of the bases adenine, cytosine, guanine, thymine, or uracil joined to the 1' carbon of .beta.-D-ribo-furanose.

By "modified nucleoside" is meant any nucleotide base which contains a modification in the chemical structure of an unmodified nucleotide base, sugar and/or phosphate. Non-limiting examples of modified nucleotides are shown by Formulae I-VII and/or other modifications described herein.

In connection with 2'-modified nucleotides as described for the present invention, by "amino" is meant 2'—$NH_2$ or 2'—O—$NH_2$, which can be modified or unmodified. Such modified groups are described, for example, in Eckstein, et al., U.S. Pat. No. 5,672,695 and Matulic-Adamic, et al., U.S. Pat. No. 6,248,878.

The siNA molecules can be complexed with cationic lipids, packaged within liposomes, or otherwise delivered to target cells or tissues. The nucleic acid or nucleic acid complexes can be locally administered to through injection, infusion pump or stent, with or without their incorporation in biopolymers. In another embodiment, polyethylene glycol (PEG) can be covalently attached to siNA compounds of the present invention. The attached PEG can be any molecular weight, preferably from about 2,000 to about 50,000 Daltons (Da).

The sense region can be connected to the antisense region via a linker molecule, such as a polynucleotide linker or a non-nucleotide linker.

EXAMPLE 1

Tight junctions (TJ) form at the apical end of lateral membranes as closed contacts between the plasma membranes of neighboring cells. The TJ serves as a diffusion barrier between compartments and it is crucial for the development and function of epithelial tissues. Previous studies have suggested that the intra-membrane connections are formed by non-covalently linked branched polymers containing Claudins (CLDNs), Occludin and Junctional Adhesion Molecules (JAMs). These transmembrane proteins interact with multiple components of a cytoplasmic plaque consisting of different types of cytosolic proteins that interact with an actin-based cytoskeleton. There are at least 20 different claudins in epithelial tissues. CLDN tissue-specific expression has been demonstrated in normal as well as in malignant epithelial tissues.

Studies of the structure and functional properties of the TJ will not only provide insight on how the barrier is formed, but will identify those components that are most amenable to functional manipulation. The ability to transiently open tight junctions will facilitate the delivery of large molecule drugs, such as peptides, for nasal drug delivery.

Experimental Methods

Cell Culture—16HBE14o- Cells were grown in collagen coated flasks in complete MEM supplemented with 10% FBS. During passage, cells were washed with PBS and detached using a low concentration of trypsin solution. For Insert seeding, cells were re-suspended in DMEM/F12 complete media. 12-well BD Falcon inserts (Becton Dickinson, Franklin Lakes, N.J.) with 0.4 µm pore size were presoaked with media. Cell suspension was then added onto the apical side and cultured for 72 hrs before transfection. TER changes were monitored to evaluate the TJ formation.

siRNA Transfection—Four hour transfections of siRNAs were conducted 72 and 96 hours after seeding cells on inserts in serum free DMEM/F12, followed by addition of complete media. Each transfection mixture contained 80 µmol of siRNA and 4 µl of Lipofectamine 2000 (Invitrogen, Carlsbad, Calif.). Cells grown in dishes were transfected at approximately 50% confluence with 100 µmol siRNA/well in 6-well plates. Cells were then allowed to grow to confluence after transfection and either harvested for insert seeding or photographed. For insert seeding with siRNA-treated cells, transfected cells were detached, counted and re-suspended prior to seeding. When over 80 µmol siRNA was used for each insert in optimal lipofectamine/siRNA ratio for transfection, cell damage was observed as indicated by MTT and LDH assays.

TER Measurement—Fresh, warm media is placed in a UV sterilized Endohm tissue resistance measurement chamber connected to an EVOM resistance meter from WPI (Sarasota, Fla.), and allowed to equilibrate to room temperature. Inserts to be measured were removed from the incubator and allowed to equilibrate to room temperature prior to measurement.

Permeability Assay—Inserts were left in the TER chamber until constant values were displayed. 50 µg of FITC dextran, MW 4,400, was applied on the apical side of each insert. Medium from basolateral chamber was transferred into 96-well plates and the amount of FITC determined by measuring fluorescence intensity following 1 hr incubation The permeability of each sample was calculated as percent of control (total fluorescence from lysed cell insert).

Immunofluorescence—Cells were either grown on collagen V coated coverslips or multi-well plates. After transfection or other treatments, cells were rinsed with PBS twice and fixed with 1% formaldehyde in PBS at room temperature for 10 min. Then 0.2% Triton X-100 was used to permeabilize cells for 10 min at room temperature. The cells were then blocked with 1% BSA for 30 min at room temperature and incubated with primary antibodies against Occludin or Claudin 4 (Zymed Inc. South San Francisco, Calif.) at room temperature for 60 min. FITC-conjugated goat anti-rabbit IgG (1:200) was used for Occludin and TRITC-conjugated goat anti-mouse (1:200) for Claudin 4 in double labeling at room temperature for 30 min. Between steps, the cells were washed 3x-PBS. Vectashield mounting medium with DAPI (Vector Laboratories, Burlingame, Calif.) were used for coverslips. The images were captured using an inverted fluorescence microscope (Nikon eclipse TE2000).

TABLE 1

Expression Profile of Claudins in Differentiated and Undifferentiated Epithelial Cells

|  |  | Undiffrentiated | | Differentiated | |
|---|---|---|---|---|---|
| Claudins | Product | TBE | RPMI 2650 | AIR | 16HBE14o- |
| CLDN-1  | 208 | ++++ | ++++ | ++++  | ++++ |
| CLDN-2  | 203 | +    | +    | —     | +    |
| CLDN-3  | 247 | —    | —    | +++++ | ++++ |
| CLDN-4  | 217 | +    | —    | ++++  | ++++ |
| CLDN-5  | 221 | +    | —    | +     | ++   |
| CLDN-6  | 150 | —    | —    | —     | —    |
| CLDN-7  | 196 | ++   | ++   | ++++  | ++++ |
| CLDN-8  | 204 | —    | —    | —     | —    |
| CLDN-9  | 225 | —    | —    | ++++  | —    |
| CLDN-10 | 238 | —    | —    | +     | +    |
| CLDN-11 | 235 | ++   | —    | ++    | +    |
| CLDN-12 | 150 | ++++ | ++++ | ++++  | ++++ |
| CLDN-14 | 235 | +    | +    | ++    | +    |
| CLON-15 | 186 | —    | —    | —     | —    |
| CLDN-16 | 204 | —    | ++   | +     | +    |
| CLDN-17 | 246 | —    | —    | —     | —    |
| CLDN-18 | 190 | —    | +    | —     | —    |
| CLDN-19 | 204 | —    | —    | —     | —    |
| CLDN-20 | 156 | ++++ | ++   | ++++  | ++   |

Scale of expression level (+) is relative to actin.
TBE - undifferentiated cells from MatTek;
Air - differentiated cells from MatTek

TABLE 2 siRNA Sequences for Tight Junction Proteins

| TJ Proteins | siRNA Target Sequence |
|---|---|
| Claudin 1   | AACCUCUUACCCAACACCAAG (SEQ ID NO: 3) |
| Claudin 3   | AAAUCACGUCGCAGAACAUUU (SEQ ID NO: 4) |
| Claudin 4   | AAGACUUCUACAAUCCGCUGG (SEQ ID NO: 5) |
| Claudin 9   | AAGGUGUACGACUCACUGCUG (SEQ ID NO: 6) |
| Claudin 12  | AAUAGUGCAGGUUGCCACCUG (SEQ ID NO: 7) |
| Claudin 20  | AAUGAAAUGUACUCGCUUAGG (SEQ ID NO: 8) |
| JAM-1       | GACCUUCUUGCCAACUGGUAU (SEQ ID NO: 9) |
| Occludin    | GAAAACUCGAAGAAAGAUGGA (SEQ ID NO: 10) |
| Negative Control | AAUUCUCCGAACGUGUCACGU (SEQ ID NO; 11) |

The siRNAs used to target the mRNA of the tight junction proteins were the following:

TABLE 3 siRNA Sequences for Tight Junction Proteins

| Targets | RNA sense sequence | Antisense sequence |
|---|---|---|
| Claudin-1  | CCUCUUACCCAACACCAAG (SEQ ID NO: 12) | GAACCACAACCCAUUCUCC (SEQ ID NO: 13) |
| Claudin-1  | GCAUGGUAUGGCAAUAGAA (SEQ ID NO: 14) | UUCUAUUGCCAUACCAUGC (SEQ ID NO: 15) |
| Claudin-3  | CAUCAUCACGUCGCAGAAC (SEQ ID NO: 16) | GUUCUGCGACGUGAUGAUG (SEQ ID NO: 17) |
| Claudin-3  | GCAAGGACUACCGUCUAUU (SEQ ID NO: 18) | AAUAGACGGUAGUCCUUGC (SEQ ID NO: 19) |
| Claudin-3  | AUCACGUCGCAGAACAUUU (SEQ ID NO: 20) | AAAUGUUCUGCGACGUGAU (SEQ ID NO: 21) |
| Claudin-4  | GACUUCUACAAUCCGCUGG (SEQ ID NO: 22) | CCAGCGGAUUGUAGAAGUC (SEQ ID NO: 23) |
| Claudin-4  | CAUCAUCCAAGACUUCUAC (SEQ ID NO: 24) | GUAGAAGUCUUGGAUGAUG (SEQ ID NO: 25) |
| Claudin-4  | GACUUCUACAAUCCGCUGG (SEQ ID NO: 26) | CCAGCGGAUUGUAGAAGUC (SEQ ID NO: 27) |
| Claudin-9  | CCCACUUUCCAAAAGCCCA (SEQ ID NO: 28) | UGGGCUUUUGGAAAGUGGG (SEQ ID NO: 29) |
| Claudin-9  | GGUGUACGACUCACUGCUG (SEQ ID NO: 30) | CAGCAGUGAGUCGUACACC (SEQ ID NO: 31) |
| Claudin-12 | UAGUGCAGGUUGCCACCUG (SEQ ID NO: 32) | CAGGUGGCAACCUGCACUA (SEQ ID NO: 33) |
| Claudin-12 | GUGACUGCCUGAUGUACGA (SEQ ID NO: 34) | UCGUACAUCAGGCAGUCAC (SEQ ID NO: 35) |
| Claudin-12 | AUGCGCAACACUGCCUUCA (SEQ ID NO: 36) | UGAAGGCAGUGUUGCGCAU (SEQ ID NO: 37) |
| Claudin-20 | AUGUACUCGCUUAGGAGGG (SEQ ID NO: 38) | CCCUCCUAAGCGAGUACAU (SEQ ID NO: 39) |
| Claudin-20 | UGAAAUGUACUCGCUUAGG (SEQ ID NO: 40) | CCUAAGCGAGUACAUUUCA (SEQ ID NO: 41) |
| Claudin-20 | CCUGGAGGAGCUAUCUAUA (SEQ ID NO: 42) | UAUAGAUAGCUCCUCCAGG (SEQ ID NO: 43) |
| Occludin   | UGGGAGUGAACCCAACUGC (SEQ ID NO: 44) | GCAGUUGGGUUCACUCCCA (SEQ ID NO: 45) |
| Occludin   | AAACUCGAAGAAAGAUGGA (SEQ ID NO: 46) | UCCAUCUUUCUUCGAGUUU (SEQ ID NO: 47) |
| Occludin   | ACAGAGCAAGAUCACUAUG (SEQ ID NO: 48) | CAUAGUGAUCUUGCUCUGU (SEQ ID NO: 49) |
| JAM-1      | UCCCACAACAGGAGAGCUG (SEQ ID NO: 50) | CAGCUCUCCUGUUGUGGGA (SEQ ID NO: 51) |
| JAM-1      | CCUUCUUGCCAACUGGUAU (SEQ ID NO: 52) | AUACCAGUUGGCAAGAAGG (SEQ ID NO: 53) |
| JAM-1      | GCCUCUGAUACUGGAGAAU (SEQ ID NO: 54) | AUUCUCCAGUAUCAGAGGC (SEQ ID NO: 55) |

The dTdT are added to 3' ends of both sense and antisense strands

SUMMARY

Claudins 3 and 4 are differentially expressed in differentiated primary (MatTeck) and immortalized tight junction-forming cells (16HBE14o-), while Claudins 1, 12 and 20 are expressed in both tight junction forming cells and non-tight junction forming cells (BET cells from MatTeck and RPMI2650, a nasal tumor epithelial cells).

At least one effective siRNA was identified for Claudins 1, 3, 4, 9, 12, 20, JAM-1, and Occludin in respiratory epithelial cells.

Claudin 4 was found to be essential to maintain tight junction integrity. Knocking down Claudin 4 expression either before or after tight junction formation resulted in a significant decrease in TER and this effect correlated with increased permeability for dextran, MW 4,400. Lesser effects on TER were observed for Occludin and JAM1, while knockdown of Claudin 12 had little effect on TER.

Knockdown of Claudin 4 affected cell phonotype (FIG. 9) as evidenced by changes in cell shape and a disorganized growth pattern. siRNA-transfected16HBE14o- cells exhibited multilayer growth compared to untransfected cells which grew as a monolayer.

When cells were transfected with siRNA against Claudin 4 in combination with either occludin or JAM-1 (40 μmol of siRNAs), the effects on TER appeared to be synergistic. In contrast, combinations with siRNA against Claudin 12 showed little effect.

The teachings of all of the references cited herein are incorporated in their entirety by reference.

What is claimed is:

1. A small interfering nucleic acid (siNA) that down-regulates the expression of a junctional adhesion molecule-1 (JAM-1) mRNA, the siNA comprising a sense strand, an antisense strand having at least 19 nucleotides, and a duplex region, wherein the nucleotide sequence of the antisense strand comprises SEQ ID NO:51.

2. The siNA of claim 1, wherein the duplex region has at least 19 base pairs.

3. The siNA of claim 1, wherein the sense strand and antisense strand each independently have from about 19 to about 1 nucleotides.

4. The siNA of claim 1, wherein the siNA has a 5'-cap and/or 3'-cap structure.

5. The siNA of claim 1, wherein the siNA has at least one 3' overhang.

6. The siNA of claim 1, wherein the siNA down-regulates the expression of a junctional adhesion molecule-1 (JAM-1) mRNA in a respiratory epithelial cell.

* * * * *

UNITED STATES PATENT AND TRADEMARK OFFICE
CERTIFICATE OF CORRECTION

PATENT NO. : 7,696,343 B2
APPLICATION NO. : 11/624630
DATED : April 13, 2010
INVENTOR(S) : Kunyuan Cui et al.

It is certified that error appears in the above-identified patent and that said Letters Patent is hereby corrected as shown below:

Column 1, line 6: After "Dec. 10, 2004," insert -- now abandoned, --.
Column 2, line 59: Delete "(80 μmol/insert)" and insert -- (80 pmol/insert). --, therefor.
Column 2, line 66: Delete "(80 μmol/each)" and insert -- (80 pmol/each) --, therefor.
Column 3, line 7: Delete "(40 μmol)" and insert -- (40 pmol) --, therefor.
Column 3, line 9: Delete "(80 μmol)" and insert -- (80 pmol) --, therefor.
Column 3, line 11: Delete "(40 μmol each)" and insert -- (40 pmol each) --, therefor.
Column 3, line 15: Delete "(40 μmol)" and insert -- (40 pmol) --, therefor.
Column 3, line 17: Delete "(80 μmol)" and insert -- (80 pmol) --, therefor.
Column 3, line 19: Delete "(40 μmol each)" and insert -- (40 pmol each) --, therefor.
Column 3, line 30: Delete "(40 μmol)" and insert -- (40 pmol) --, therefor.
Column 3, line 32: Delete "(80 μmol)" and insert -- (80 pmol) --, therefor.
Column 3, line 34: Delete "(40 μmol each)" and insert -- (40 pmol each) --, therefor
Column 3, line 35: Delete "80 μmol" and insert -- 80 pmol --, therefor.
Column 7, line 56: Delete "Berstein, et al.," and insert -- Bernstein, et al., --, therefor.
Column 10, line 25: Delete "micleotides." and insert -- nucleotides, --, therefor.
Column 23, line 15: After "or" insert -- 20 --.
Column 24, line 26: Delete "80 μmol" and insert -- 80 pmol --, therefor.
Column 24, line 29: Delete "100 μmol" and insert -- 100 pmol --, therefor.
Column 24, line 34: Delete "80 μmol" and insert -- 80 pmol --, therefor.
Column 25, line 6: Delete "Undiffrentiated" and insert -- Undifferentiated --, therefor.
Column 45, line 64: In Claim 3, delete "1" and insert -- 25 --, therefor.
Column 46, line 61: In Claim 6, delete "rnRNA" and insert -- mRNA --, therefor.

Signed and Sealed this

Fifth Day of October, 2010

David J. Kappos
*Director of the United States Patent and Trademark Office*

SEQUENCE LISTING

```
<160> NUMBER OF SEQ ID NOS: 56

<210> SEQ ID NO 1
<211> LENGTH: 299
<212> TYPE: PRT
<213> ORGANISM: Homo sapiens

<400> SEQUENCE: 1

Met Gly Thr Lys Ala Gln Val Glu Arg Lys Leu Leu Cys Leu Phe Ile
1               5                   10                  15

Leu Ala Ile Leu Leu Cys Ser Leu Ala Leu Gly Ser Val Thr Val His
                20                  25                  30

Ser Ser Glu Pro Glu Val Arg Ile Pro Glu Asn Asn Pro Val Lys Leu
            35                  40                  45

Ser Cys Ala Tyr Ser Gly Phe Ser Ser Pro Arg Val Glu Trp Lys Phe
        50                  55                  60

Asp Gln Gly Asp Thr Thr Arg Leu Val Cys Tyr Asn Asn Lys Ile Thr
65                  70                  75                  80

Ala Ser Tyr Glu Asp Arg Val Thr Phe Leu Pro Thr Gly Ile Thr Phe
                85                  90                  95

Lys Ser Val Thr Arg Glu Asp Thr Gly Thr Tyr Thr Cys Met Val Ser
            100                 105                 110

Glu Glu Gly Gly Asn Ser Tyr Gly Glu Val Lys Val Lys Leu Ile Val
        115                 120                 125

Leu Val Pro Pro Ser Lys Pro Thr Val Asn Ile Pro Ser Ser Ala Thr
    130                 135                 140

Ile Gly Asn Arg Ala Val Leu Thr Cys Ser Glu Gln Asp Gly Ser Pro
145                 150                 155                 160

Pro Ser Glu Tyr Thr Trp Phe Lys Asp Gly Ile Val Met Pro Thr Asn
                165                 170                 175

Pro Lys Ser Thr Arg Ala Phe Ser Asn Ser Ser Tyr Val Leu Asn Pro
            180                 185                 190

Thr Thr Gly Glu Leu Val Phe Asp Pro Leu Ser Ala Ser Asp Thr Gly
        195                 200                 205

Glu Tyr Ser Cys Glu Ala Arg Asn Gly Tyr Gly Thr Pro Met Thr Ser
    210                 215                 220

Asn Ala Val Arg Met Glu Ala Val Glu Arg Asn Val Gly Val Ile Val
225                 230                 235                 240

Ala Ala Val Leu Val Thr Leu Ile Leu Leu Gly Ile Leu Val Phe Gly
                245                 250                 255

Ile Trp Phe Ala Tyr Ser Arg Gly His Phe Asp Arg Thr Lys Lys Gly
            260                 265                 270
```

```
Thr Ser Ser Lys Lys Val Ile Tyr Ser Gln Pro Ser Ala Arg Ser Glu
        275                 280                 285

Gly Glu Phe Lys Gln Thr Ser Ser Phe Leu Val
    290                 295

<210> SEQ ID NO 2
<211> LENGTH: 209
<212> TYPE: PRT
<213> ORGANISM: Homo sapiens

<400> SEQUENCE: 2

Met Ala Ser Met Gly Leu Gln Val Met Gly Ile Ala Leu Ala Val Leu
  1               5                  10                  15

Gly Trp Leu Ala Val Met Leu Cys Cys Ala Leu Pro Met Trp Arg Val
             20                  25                  30

Thr Ala Phe Ile Gly Ser Asn Ile Val Thr Ser Gln Thr Ile Trp Glu
         35                  40                  45

Gly Leu Trp Met Asn Cys Val Val Gln Ser Thr Gly Gln Met Gln Cys
     50                  55                  60

Lys Val Tyr Asp Ser Leu Leu Ala Leu Pro Gln Asp Leu Gln Ala Ala
 65                  70                  75                  80

Arg Ala Leu Val Ile Ile Ser Ile Ile Val Ala Ala Leu Gly Val Leu
                 85                  90                  95

Leu Ser Val Val Gly Gly Lys Cys Thr Asn Cys Leu Glu Asp Glu Ser
            100                 105                 110

Ala Lys Ala Lys Thr Met Ile Val Ala Gly Val Val Phe Leu Leu Ala
        115                 120                 125

Gly Leu Met Val Ile Val Pro Val Ser Trp Thr Ala His Asn Ile Ile
    130                 135                 140

Gln Asp Phe Tyr Asn Pro Leu Val Ala Ser Gly Gln Lys Arg Glu Met
145                 150                 155                 160

Gly Ala Ser Leu Tyr Val Gly Trp Ala Ala Ser Gly Leu Leu Leu Leu
                165                 170                 175

Gly Gly Gly Leu Leu Cys Cys Asn Cys Pro Pro Arg Thr Asp Lys Pro
            180                 185                 190

Tyr Ser Ala Lys Tyr Ser Ala Ala Arg Ser Ala Ala Ala Ser Asn Tyr
        195                 200                 205

Val

<210> SEQ ID NO 3
<211> LENGTH: 21
<212> TYPE: RNA
<213> ORGANISM: Homo sapiens

<400> SEQUENCE: 3
aaccucuuac ccaacaccaa g                                          21

<210> SEQ ID NO 4
<211> LENGTH: 21
<212> TYPE: RNA
<213> ORGANISM: Homo sapiens

<400> SEQUENCE: 4
aaaucacguc gcagaacauu u                                          21

<210> SEQ ID NO 5
<211> LENGTH: 21
<212> TYPE: RNA
```

<213> ORGANISM: Homo sapiens

<400> SEQUENCE: 5
aagacuucua caauccgcug g              21

<210> SEQ ID NO 6
<211> LENGTH: 21
<212> TYPE: RNA
<213> ORGANISM: Homo sapiens

<400> SEQUENCE: 6
aagguguacg acucacugcu g              21

<210> SEQ ID NO 7
<211> LENGTH: 21
<212> TYPE: RNA
<213> ORGANISM: Homo sapiens

<400> SEQUENCE: 7
aauagugcag guugccaccu g              21

<210> SEQ ID NO 8
<211> LENGTH: 21
<212> TYPE: RNA
<213> ORGANISM: Homo sapiens

<400> SEQUENCE: 8
aaugaaaugu acucgcuuag g              21

<210> SEQ ID NO 9
<211> LENGTH: 21
<212> TYPE: RNA
<213> ORGANISM: Homo sapiens

<400> SEQUENCE: 9
gaccuucuug ccaacuggua u              21

<210> SEQ ID NO 10
<211> LENGTH: 21
<212> TYPE: RNA
<213> ORGANISM: Homo sapiens

<400> SEQUENCE: 10
gaaaacucga agaaagaugg a              21

<210> SEQ ID NO 11
<211> LENGTH: 21
<212> TYPE: RNA
<213> ORGANISM: Homo sapiens

<400> SEQUENCE: 11
aauucuccga acgugucacg u              21

<210> SEQ ID NO 12
<211> LENGTH: 19
<212> TYPE: RNA
<213> ORGANISM: Homo sapiens

<400> SEQUENCE: 12
ccucuuaccc aacaccaag              19

<210> SEQ ID NO 13
<211> LENGTH: 19

```
<212> TYPE: RNA
<213> ORGANISM: Homo sapiens

<400> SEQUENCE: 13
gaaccacaac ccauucucc                                                 19

<210> SEQ ID NO 14
<211> LENGTH: 19
<212> TYPE: RNA
<213> ORGANISM: Homo sapiens

<400> SEQUENCE: 14
gcaugguaug gcaauagaa                                                 19

<210> SEQ ID NO 15
<211> LENGTH: 19
<212> TYPE: RNA
<213> ORGANISM: Homo sapiens

<400> SEQUENCE: 15
uucuauugcc auaccaugc                                                 19

<210> SEQ ID NO 16
<211> LENGTH: 19
<212> TYPE: RNA
<213> ORGANISM: Homo sapiens

<400> SEQUENCE: 16
caucaucacg ucgcagaac                                                 19

<210> SEQ ID NO 17
<211> LENGTH: 19
<212> TYPE: RNA
<213> ORGANISM: Homo sapiens

<400> SEQUENCE: 17
guucugcgac gugaugaug                                                 19

<210> SEQ ID NO 18
<211> LENGTH: 19
<212> TYPE: RNA
<213> ORGANISM: Homo sapiens

<400> SEQUENCE: 18
gcaaggacua ccgucuauu                                                 19

<210> SEQ ID NO 19
<211> LENGTH: 19
<212> TYPE: RNA
<213> ORGANISM: Homo sapiens

<400> SEQUENCE: 19
aauagacggu aguccuugc                                                 19

<210> SEQ ID NO 20
<211> LENGTH: 19
<212> TYPE: RNA
<213> ORGANISM: Homo sapiens

<400> SEQUENCE: 20
aucacgucgc agaacauuu                                                 19

<210> SEQ ID NO 21
```

```
<211> LENGTH: 19
<212> TYPE: RNA
<213> ORGANISM: Homo sapiens

<400> SEQUENCE: 21 aauguucug cgacgugau                                                  19

<210> SEQ ID NO 22
<211> LENGTH: 19
<212> TYPE: RNA
<213> ORGANISM: Homo sapiens

<400> SEQUENCE: 22
gacuucuaca auccgcugg                                                 19

<210> SEQ ID NO 23
<211> LENGTH: 19
<212> TYPE: RNA
<213> ORGANISM: Homo sapiens

<400> SEQUENCE: 23
ccagcggauu guagaaguc                                                 19

<210> SEQ ID NO 24
<211> LENGTH: 19
<212> TYPE: RNA
<213> ORGANISM: Homo sapiens

<400> SEQUENCE: 24
caucauccaa gacuucuac                                                 19

<210> SEQ ID NO 25
<211> LENGTH: 19
<212> TYPE: RNA
<213> ORGANISM: Homo sapiens

<400> SEQUENCE: 25
guagaagucu uggaugaug                                                 19

<210> SEQ ID NO 26
<211> LENGTH: 19
<212> TYPE: RNA
<213> ORGANISM: Homo sapiens

<400> SEQUENCE: 26
gacuucuaca auccgcugg                                                 19

<210> SEQ ID NO 27
<211> LENGTH: 19
<212> TYPE: RNA
<213> ORGANISM: Homo sapiens

<400> SEQUENCE: 27
ccagcggauu guagaaguc                                                 19

<210> SEQ ID NO 28
<211> LENGTH: 19
<212> TYPE: RNA
<213> ORGANISM: Homo sapiens

<400> SEQUENCE: 28
cccacuuucc aaaagccca                                                 19
```

```
<210> SEQ ID NO 29
<211> LENGTH: 19
<212> TYPE: RNA
<213> ORGANISM: Homo sapiens

<400> SEQUENCE: 29
ugggcuuuug gaaaguggg                                                      19

<210> SEQ ID NO 30
<211> LENGTH: 19
<212> TYPE: RNA
<213> ORGANISM: Homo sapiens

<400> SEQUENCE: 30
gguguacgac ucacugcug                                                      19

<210> SEQ ID NO 31
<211> LENGTH: 19
<212> TYPE: RNA
<213> ORGANISM: Homo sapiens

<400> SEQUENCE: 31
cagcagugag ucguacacc                                                      19

<210> SEQ ID NO 32
<211> LENGTH: 19
<212> TYPE: RNA
<213> ORGANISM: Homo sapiens

<400> SEQUENCE: 32
uagugcaggu ugccaccug                                                      19

<210> SEQ ID NO 33
<211> LENGTH: 19
<212> TYPE: RNA
<213> ORGANISM: Homo sapiens

<400> SEQUENCE: 33
cagguggcaa ccugcacua                                                      19

<210> SEQ ID NO 34
<211> LENGTH: 19
<212> TYPE: RNA
<213> ORGANISM: Homo sapiens

<400> SEQUENCE: 34
gugacugccu gauguacga                                                      19

<210> SEQ ID NO 35
<211> LENGTH: 19
<212> TYPE: RNA
<213> ORGANISM: Homo sapiens

<400> SEQUENCE: 35
ucguacauca ggcagucac                                                      19

<210> SEQ ID NO 36
<211> LENGTH: 19
<212> TYPE: RNA
<213> ORGANISM: Homo sapiens

<400> SEQUENCE: 36
augcgcaaca cugccuuca                                                      19
```

```
<210> SEQ ID NO 37
<211> LENGTH: 19
<212> TYPE: RNA
<213> ORGANISM: Homo sapiens

<400> SEQUENCE: 37
ugaaggcagu guugcgcau                                                  19

<210> SEQ ID NO 38
<211> LENGTH: 19
<212> TYPE: RNA
<213> ORGANISM: Homo sapiens

<400> SEQUENCE: 38
auguacucgc uuaggaggg                                                  19

<210> SEQ ID NO 39
<211> LENGTH: 19
<212> TYPE: RNA
<213> ORGANISM: Homo sapiens

<400> SEQUENCE: 39
cccuccuaag cgaguacau                                                  19

<210> SEQ ID NO 40
<211> LENGTH: 19
<212> TYPE: RNA
<213> ORGANISM: Homo sapiens

<400> SEQUENCE: 40
ugaaauguac ucgcuuagg                                                  19

<210> SEQ ID NO 41
<211> LENGTH: 19
<212> TYPE: RNA
<213> ORGANISM: Homo sapiens

<400> SEQUENCE: 41
ccuaagcgag uacauuuca                                                  19

<210> SEQ ID NO 42
<211> LENGTH: 19
<212> TYPE: RNA
<213> ORGANISM: Homo sapiens

<400> SEQUENCE: 42
ccuggaggag cuaucuaua                                                  19

<210> SEQ ID NO 43
<211> LENGTH: 19
<212> TYPE: RNA
<213> ORGANISM: Homo sapiens

<400> SEQUENCE: 43
uauagauagc uccuccagg                                                  19

<210> SEQ ID NO 44
<211> LENGTH: 19
<212> TYPE: RNA
<213> ORGANISM: Homo sapiens

<400> SEQUENCE: 44
ugggagugaa cccaacugc                                                  19
```

<210> SEQ ID NO 45
<211> LENGTH: 19
<212> TYPE: RNA
<213> ORGANISM: Homo sapiens

<400> SEQUENCE: 45
gcaguggggu ucacuccca                                                    19

<210> SEQ ID NO 46
<211> LENGTH: 19
<212> TYPE: RNA
<213> ORGANISM: Homo sapiens

<400> SEQUENCE: 46
aaacucgaag aaagaugga                                                    19

<210> SEQ ID NO 47
<211> LENGTH: 19
<212> TYPE: RNA
<213> ORGANISM: Homo sapiens

<400> SEQUENCE: 47
uccaucuuuc uucgaguuu                                                    19

<210> SEQ ID NO 48
<211> LENGTH: 19
<212> TYPE: RNA
<213> ORGANISM: Homo sapiens

<400> SEQUENCE: 48
acagagcaag aucacuaug                                                    19

<210> SEQ ID NO 49
<211> LENGTH: 19
<212> TYPE: RNA
<213> ORGANISM: Homo sapiens

<400> SEQUENCE: 49
cauagugauc uugcucugu                                                    19

<210> SEQ ID NO 50
<211> LENGTH: 19
<212> TYPE: RNA
<213> ORGANISM: Homo sapiens

<400> SEQUENCE: 50
ucccacaaca ggagagcug                                                    19

<210> SEQ ID NO 51
<211> LENGTH: 19
<212> TYPE: RNA
<213> ORGANISM: Homo sapiens

<400> SEQUENCE: 51
cagcucuccu guguggga                                                     19

<210> SEQ ID NO 52
<211> LENGTH: 19
<212> TYPE: RNA
<213> ORGANISM: Homo sapiens

<400> SEQUENCE: 52
ccuucuugcc aacugguau                                                           19

<210> SEQ ID NO 53
<211> LENGTH: 19
<212> TYPE: RNA
<213> ORGANISM: Homo sapiens

<400> SEQUENCE: 53
auaccaguug gcaagaagg                                                           19

<210> SEQ ID NO 54
<211> LENGTH: 19
<212> TYPE: RNA
<213> ORGANISM: Homo sapiens

<400> SEQUENCE: 54
gccucugaua cuggagaau                                                           19

<210> SEQ ID NO 55
<211> LENGTH: 19
<212> TYPE: RNA
<213> ORGANISM: Homo sapiens

<400> SEQUENCE: 55
auucuccagu aucagaggc                                                           19

<210> SEQ ID NO 56
<211> LENGTH: 522
<212> TYPE: PRT
<213> ORGANISM: Homo sapiens

<400> SEQUENCE: 56

Met Ser Ser Arg Pro Leu Glu Ser Pro Pro Tyr Arg Pro Asp Glu
  1               5                  10                  15

Phe Lys Pro Asn His Tyr Ala Pro Ser Asn Asp Ile Tyr Gly Gly Glu
                 20                  25                  30

Met His Val Arg Pro Met Leu Ser Gln Pro Ala Tyr Ser Phe Tyr Pro
             35                  40                  45

Glu Asp Glu Ile Leu His Phe Tyr Lys Trp Thr Ser Pro Pro Gly Val
 50                  55                  60

Ile Arg Ile Leu Ser Met Leu Ile Ile Val Met Cys Ile Ala Ile Phe
 65                  70                  75                  80

Ala Cys Val Ala Ser Thr Leu Ala Trp Asp Arg Gly Tyr Gly Thr Ser
                 85                  90                  95

Leu Leu Gly Gly Ser Val Gly Tyr Pro Tyr Gly Gly Ser Gly Phe Gly
            100                 105                 110

Ser Tyr Gly Ser Gly Tyr Gly Tyr Gly Tyr Gly Tyr Gly Tyr Gly Tyr
            115                 120                 125

Gly Gly Tyr Thr Asp Pro Arg Ala Ala Lys Gly Phe Met Leu Ala Met
        130                 135                 140

Ala Ala Phe Cys Phe Ile Ala Ala Leu Val Ile Phe Val Thr Ser Val
145                 150                 155                 160

Ile Arg Ser Glu Met Ser Arg Thr Arg Arg Tyr Tyr Leu Ser Val Ile
                165                 170                 175

Ile Val Ser Ala Ile Leu Gly Ile Met Val Phe Ile Ala Thr Ile Val
            180                 185                 190

Tyr Ile Met Gly Val Asn Pro Thr Ala Gln Ser Ser Gly Ser Leu Tyr
        195                 200                 205

```
Gly Ser Gln Ile Tyr Ala Leu Cys Asn Gln Phe Tyr Thr Pro Ala Ala
    210                 215                 220
Thr Gly Leu Tyr Val Asp Gln Tyr Leu Tyr His Tyr Cys Val Val Asp
225                 230                 235                 240
Pro Gln Glu Ala Ile Ala Ile Val Leu Gly Phe Met Ile Ile Val Ala
                245                 250                 255
Phe Ala Leu Ile Ile Phe Phe Ala Val Lys Thr Arg Arg Lys Met Asp
                260                 265                 270
Arg Tyr Asp Lys Ser Asn Ile Leu Trp Asp Lys Glu His Ile Tyr Asp
            275                 280                 285
Glu Gln Pro Pro Asn Val Glu Glu Trp Val Lys Asn Val Ser Ala Gly
    290                 295                 300
Thr Gln Asp Val Pro Ser Pro Ser Asp Tyr Val Glu Arg Val Asp
305                 310                 315                 320
Ser Pro Met Ala Tyr Ser Ser Asn Gly Lys Val Asn Asp Lys Arg Phe
                325                 330                 335
Tyr Pro Glu Ser Ser Tyr Lys Ser Thr Pro Val Pro Glu Val Val Gln
            340                 345                 350
Glu Leu Pro Leu Thr Ser Pro Val Asp Asp Phe Arg Gln Pro Arg Tyr
        355                 360                 365
Ser Ser Gly Gly Asn Phe Glu Thr Pro Ser Lys Arg Ala Pro Ala Lys
    370                 375                 380
Gly Arg Ala Gly Arg Ser Lys Arg Thr Glu Gln Asp His Tyr Glu Thr
385                 390                 395                 400
Asp Tyr Thr Thr Gly Gly Glu Ser Cys Asp Glu Leu Glu Glu Asp Trp
                405                 410                 415
Ile Arg Glu Tyr Pro Pro Ile Thr Ser Asp Gln Arg Gln Leu Tyr
            420                 425                 430
Lys Arg Asn Phe Asp Thr Gly Leu Gln Glu Tyr Lys Ser Leu Gln Ser
        435                 440                 445
Glu Leu Asp Glu Ile Asn Lys Glu Leu Ser Arg Leu Asp Lys Glu Leu
    450                 455                 460
Asp Asp Tyr Arg Glu Glu Ser Glu Glu Tyr Met Ala Ala Ala Asp Glu
465                 470                 475                 480
Tyr Asn Arg Leu Lys Gln Val Lys Gly Ser Ala Asp Tyr Lys Ser Lys
            485                 490                 495
Lys Asn His Cys Lys Gln Leu Lys Ser Lys Leu Ser His Ile Lys Lys
        500                 505                 510
Met Val Gly Asp Tyr Asp Arg Gln Lys Thr
    515                 520
```